US010660395B2

(12) United States Patent
Kim et al.

(10) Patent No.: US 10,660,395 B2
(45) Date of Patent: May 26, 2020

(54) SMART TERMINAL SERVICE SYSTEM AND SMART TERMINAL PROCESSING DATA

(71) Applicant: LG ELECTRONICS INC., Seoul (KR)

(72) Inventors: Jaedong Kim, Seoul (KR); Taegil Cho, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 220 days.

(21) Appl. No.: 15/812,987

(22) Filed: Nov. 14, 2017

(65) Prior Publication Data

US 2018/0132560 A1     May 17, 2018

(30) Foreign Application Priority Data

Nov. 16, 2016    (KR) .......................... 10-2016-0152423

(51) Int. Cl.
| | |
|---|---|
| *A43B 3/00* | (2006.01) |
| *G08C 17/02* | (2006.01) |
| *G01C 22/00* | (2006.01) |
| *H04Q 9/00* | (2006.01) |
| *A43B 5/00* | (2006.01) |

(Continued)

(52) U.S. Cl.
CPC .......... *A43B 3/0005* (2013.01); *G01C 22/006* (2013.01); *G08C 17/02* (2013.01); *H04Q 9/00* (2013.01); *A43B 3/0031* (2013.01); *A43B 5/00* (2013.01); *G08C 2201/51* (2013.01); *G08C 2201/93* (2013.01); *H04L 67/12* (2013.01); *H04M 1/7253* (2013.01); *H04Q 2209/823* (2013.01); *H04Q 2213/13175* (2013.01)

(58) Field of Classification Search
CPC .......................... A43B 3/0005; G01C 22/006
USPC ......................................................... 702/160
See application file for complete search history.

(56) References Cited

U.S. PATENT DOCUMENTS

| | | | | |
|---|---|---|---|---|
| 8,280,681 B2 * | 10/2012 | Vock | .................... | A43B 3/0005 702/173 |
| 8,392,735 B2 * | 3/2013 | Mucignat | .............. | G06F 1/3203 713/323 |

(Continued)

FOREIGN PATENT DOCUMENTS

WO     WO-2015127056 A2 *    8/2015    ............. G06F 1/163

*Primary Examiner* — Ricky Ngon
(74) *Attorney, Agent, or Firm* — Lee, Hong, Degerman, Kang & Waimey

(57) ABSTRACT

A terminal service system and a terminal processing data are disclosed. The terminal service system comprises a terminal and shoe performing data communication with the terminal, wherein the shoe comprises a communication unit for transmitting and receiving a signal to and from the terminal; a sensor unit for sensing first movement data of a user who wears the shoe, through a first sensor; a memory for storing data sensed through the sensor unit; and a controller for controlling turn-on/turn-off of a second sensor on the basis of the first movement data sensed through the first sensor included in the sensor unit to sense second movement data of the user who wears the shoe, and identifying the first movement data sensed through the first sensor from the second movement data sensed through the second sensor to transmit the identified result to the smart terminal, and the smart terminal configures and outputs a user interface on the basis of the first and second movement data transmitted from the shoe.

10 Claims, 32 Drawing Sheets

(51) Int. Cl.
*H04L 29/08* (2006.01)
*H04M 1/725* (2006.01)

(56) References Cited

U.S. PATENT DOCUMENTS

| | | | | |
|---|---|---|---|---|
| 2008/0203144 A1* | 8/2008 | Kim | ............. | A61B 5/00 235/105 |
| 2015/0182844 A1* | 7/2015 | Jang | ............. | G01G 19/50 700/91 |
| 2018/0054663 A1* | 2/2018 | Markison | ............. | A61B 5/02055 |

* cited by examiner

FIG. 7
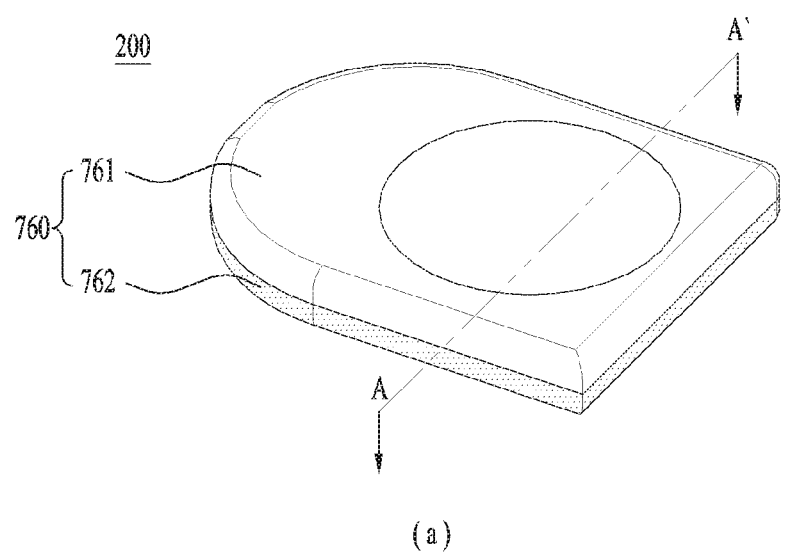
(a)
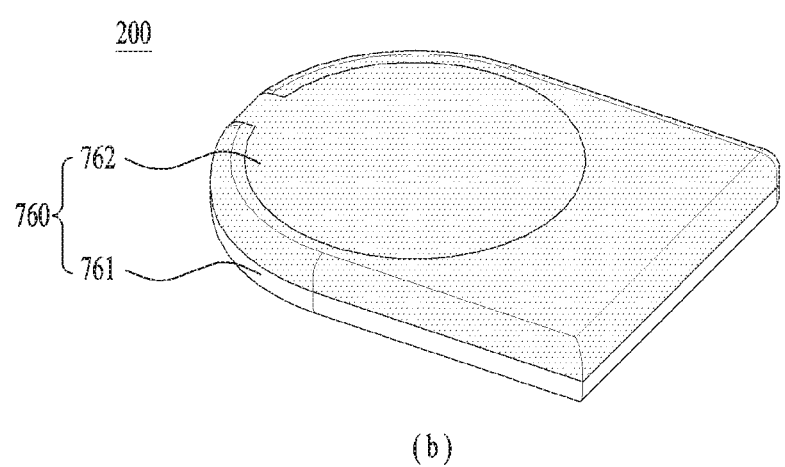
(b)

On (value of threshold pressure or more) signal measured by pressure sensor

On (ground support) signal measured by motion sensor

| | | left smart shoe | right smart shoe |
|---|---|---|---|
| measurement | pressure sensor | 0.9 | 1.1 |
| | motion sensor | 0.8 | 1.2 |

| | calibration algorithm |
|---|---|
| left smart shoe value A measured by pressure sensor | A * 0.8/0.9 |
| left smart shoe value B measured by pressure sensor | B * 1.2/1.1 |

(a)  (b)

FIG. 23
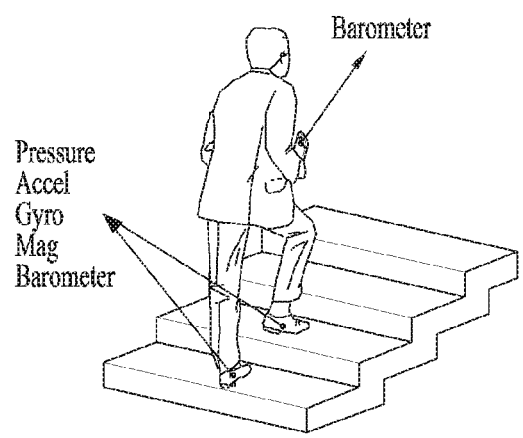 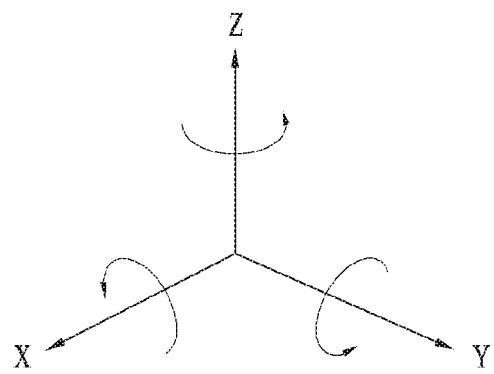
(a)  (b)

FIG. 30
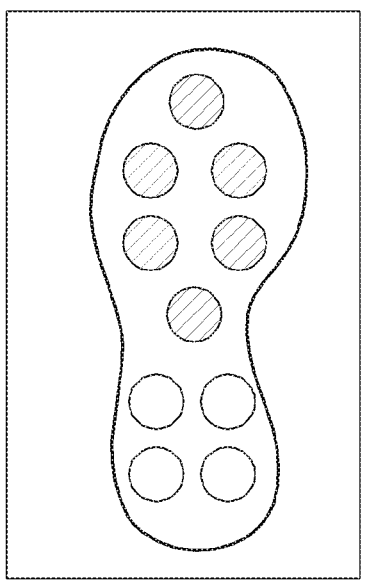
(a)
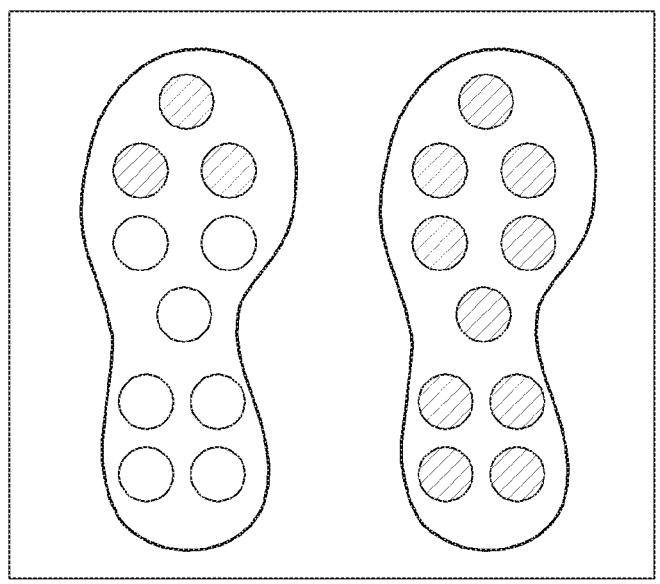
(b)

FIG. 31
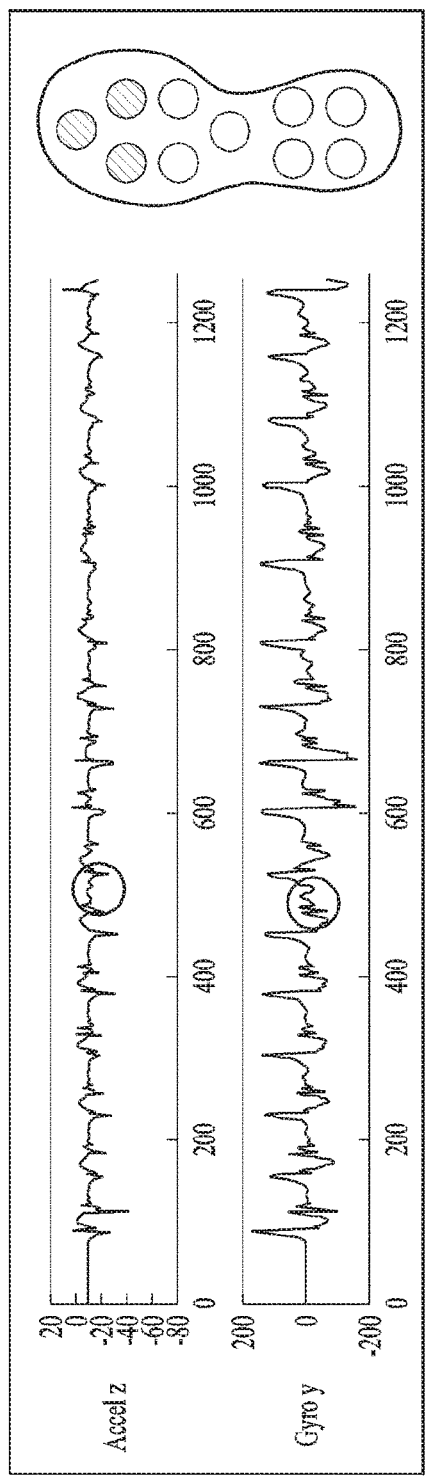
(a)
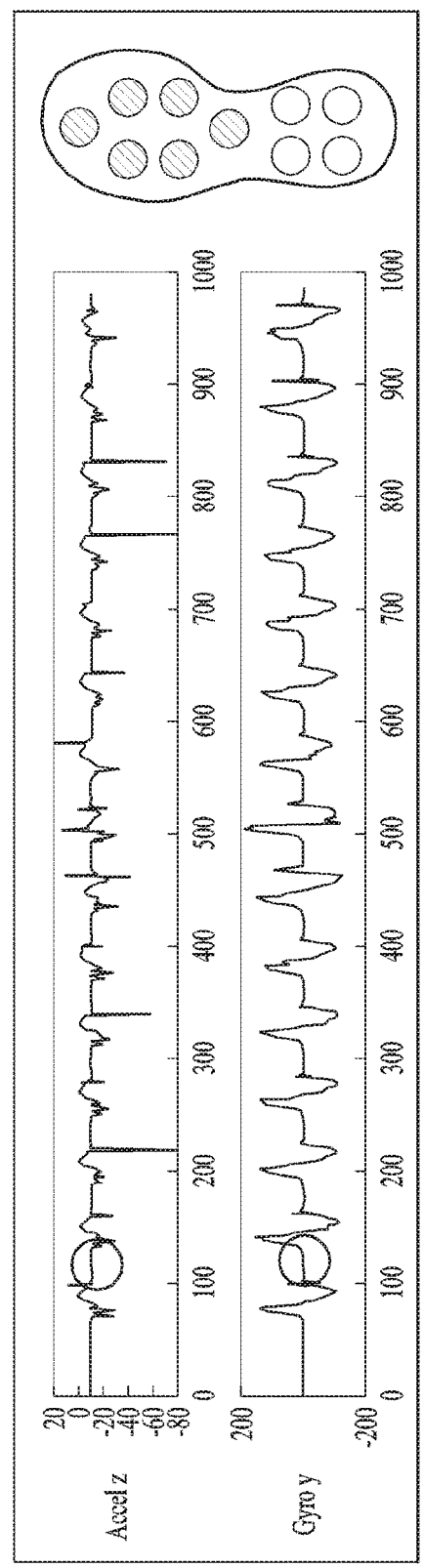
(b)

FIG. 32
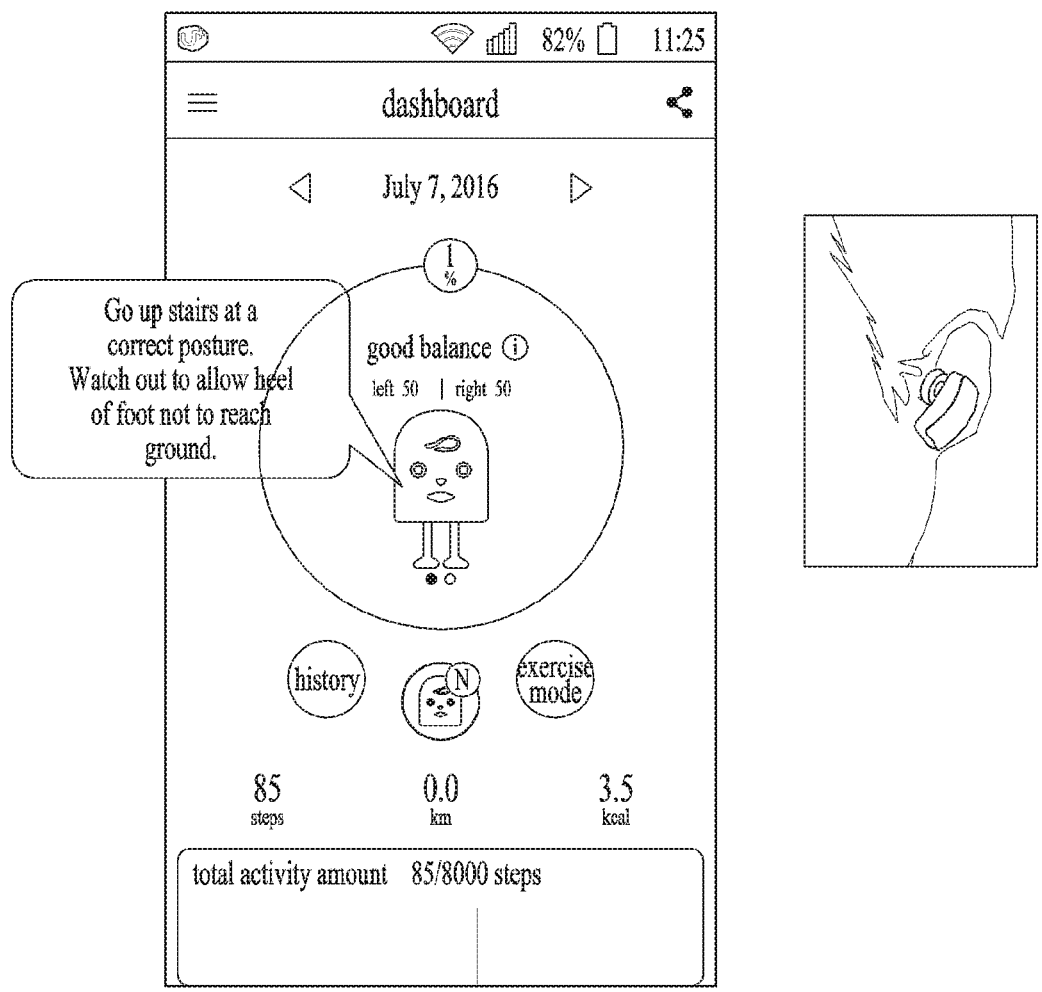
(a)
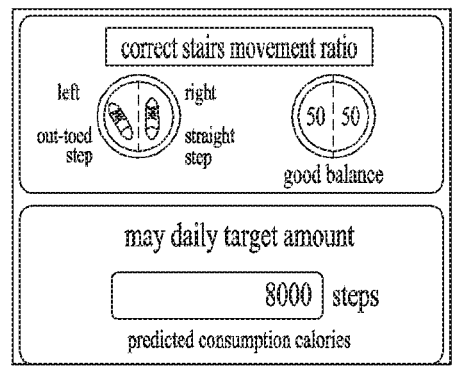
(b)

SMART TERMINAL SERVICE SYSTEM AND SMART TERMINAL PROCESSING DATA

CROSS-REFERENCE TO RELATED APPLICATIONS

Pursuant to 35 U.S.C. § 119(a), this application claims the benefit of earlier filing date and right of priority to Korean Application No. 10-2016-0152423, filed on Nov. 16, 2016, the contents of which are all hereby incorporated by reference herein in its entirety.

BACKGROUND OF THE INVENTION

Field of the Invention

The present invention relates to a smart terminal service system and a smart terminal processing data.

Discussion of the Related Art

A mobile terminal has been implemented as a multimedia player having diverse functions in addition to a simple communication function of the related art. A main example of the mobile terminal may include a smart phone. In addition, the mobile terminal has been upgraded or developed to a user wearable type, for example, a wearable device. In this case, the wearable device includes products such as clothes and shoes, which are worn by a user, as well as products such as a smart watch, a smart glass, a head mounted display (HMD).

Meanwhile, the mobile terminal leads implementation of IoT (Internet of Things) through data communication with various things together with or separately from a conventional stationary terminal.

Recently, various devices such as smart watch or smart shoes, which measure activity amount of a user, have been introduced in the market. The devices measure a total activity amount of a user in a daily unit and notify the user of the total activity amount. However, although the user performs various movements which become a basis of measurement for activity amount, the devices of the related art may fail to measure the corresponding movements or regard the movements as one movement. For example, the user may walk on a flatland or go up and down stairs as various movements. It is general that the devices of the related art may fail to identify walking on the flatland from going up and down stairs, or may recognize these movements as the same movement. Therefore, an error exists in calculation of activity amount through the devices of the related art. A problem occurs in that such an error may cause a gap between activity actually felt by a user and activity measured through the devices of the related art to affect reliability of the devices.

SUMMARY OF THE INVENTION

Accordingly, the present invention is to address the above-noted and other problems.

An object of the present invention is to exactly calculate movement data for activity of a user who wears smart shoes.

Another object of the present invention is to identify stairs movement of a user who wears smart shoes from flatland movement of the user and thus calculate exact activity amount of the user.

Other object of the present invention is to provide calculate activity amount by exactly detecting movement data of a user who wears smart shoes and provide motion guide data based on the detected movement data and calculated activity amount, thereby improving satisfaction of the user and improving reliability of the smart shoes.

The technical objects that can be achieved through the present invention are not limited to what has been particularly described hereinabove and other technical objects not described herein will be more clearly understood by persons skilled in the art from the following detailed description.

This specification discloses a smart terminal service system and a smart terminal processing data according to the present invention.

To achieve these objects and other advantages and in accordance with the purpose of the specification, as embodied and broadly described herein, smart shoes comprise a communication unit for transmitting and receiving a signal to and from an external device; a sensor unit for sensing first movement data of a user who wears the smart shoes, through a first sensor; a memory for storing data sensed through the sensor unit; and a controller for controlling turn-on/turn-off of a second sensor on the basis of the first movement data sensed through the first sensor included in the sensor unit to sense second movement data of the user who wears the smart shoes.

In another aspect of the present invention, a smart terminal service system comprises a smart terminal and smart shoes performing data communication with the smart terminal, wherein the smart shoes comprises a communication unit for transmitting and receiving a signal to and from the smart terminal; a sensor unit for sensing first movement data of a user who wears the smart shoes, through a first sensor; a memory for storing data sensed through the sensor unit; and a controller for controlling turn-on/turn-off of a second sensor on the basis of the first movement data sensed through the first sensor included in the sensor unit to sense second movement data of the user who wears the smart shoes, and identifying the first movement data sensed through the first sensor from the second movement data sensed through the second sensor to transmit the identified result to the smart terminal, and the smart terminal configures and outputs a user interface on the basis of the first and second movement data transmitted from the smart shoes.

The above technical solutions are merely some parts of the embodiments of the present invention and various embodiments into which the technical features of the present invention are incorporated can be derived and understood by persons skilled in the art from the following detailed description of the present invention.

According to the present invention, the following advantageous effects can be obtained.

According to at least one of the embodiments of the present invention, movement data for activity of a user who wears smart shoes can be calculated exactly.

According to at least one of the embodiments of the present invention, stairs movement of a user who wears smart shoes can be identified from flatland movement of the user, whereby exact activity amount of the user can be calculated.

According to at least one of the embodiments of the present invention, movement data of a user who wears smart shoes can be detected exactly to calculate activity amount, and motion guide data can be provided based on the detected movement data and the calculated activity amount, whereby satisfaction of the user can be improved and reliability of the smart shoes can be improved.

The effects that can be achieved through the present invention are not limited to what has been particularly described hereinabove and other effects not described herein will be more clearly understood by persons skilled in the art from the following detailed description.

BRIEF DESCRIPTION OF THE DRAWINGS

The present invention will become more fully understood from the detailed description given herein below and the accompanying drawings, which are given by illustration only, and thus are not limitative of the present invention, and wherein:

FIG. 7 is a view illustrating an example of an external appearance of a smart shoes sensor module 200 including a circuit configuration of FIG. 6;

FIG. 23 is a view illustrating sensors or sensor combination for stairs movement sensing related to the present invention;

FIG. 30 is a view illustrating a method for correcting movement of a user on the basis of data sensed through a sensor of smart shoes in accordance with one embodiment of the present invention;

FIG. 31 is a view illustrating a comparison of sensing data through an acceleration sensor, a gyro sensor and a pressure sensor, which are implemented in smart shoes in accordance with one embodiment of the present invention;

FIG. 32 is a view illustrating one example of a user interface provided by a smart terminal on the basis of smart shoes data in accordance with one embodiment of the present invention;

DETAILED DESCRIPTION OF THE PREFERRED EMBODIMENTS

Figure 1:
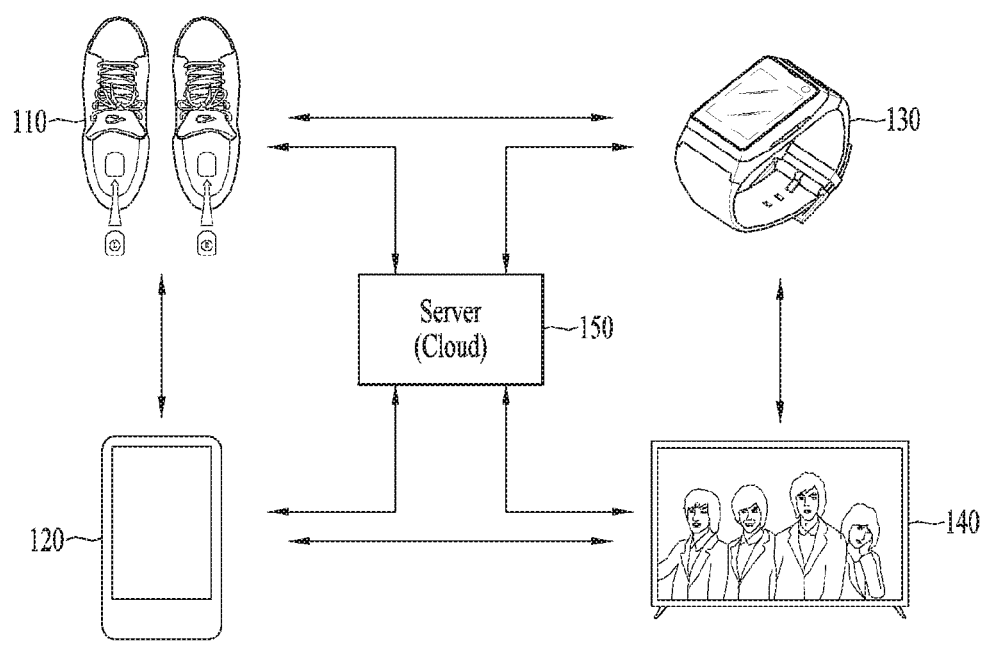
FIG. 1 is a view briefly illustrating a smart terminal service system that includes smart shoes according to one embodiment of the present invention.

Description will now be given in detail according to exemplary embodiments disclosed herein, with reference to the accompanying drawings. For the sake of brief description with reference to the drawings, the same or equivalent components may be provided with the same reference numbers, and description thereof will not be repeated.

The suffixes "module" and "unit" for the elements used in the following description are given or used in common by considering facilitation in writing this disclosure only but fail to have meanings or roles discriminated from each other.

Also, in description of the embodiments disclosed in this specification, if detailed description of the disclosure known in respect of the present invention is determined to make the subject matter of the embodiments disclosed in this specification obscure, the detailed description will be omitted. Also, the accompanying drawings are only intended to facilitate understanding of the embodiments disclosed in this specification, and it is to be understood that technical spirits disclosed in this specification are not limited by the accompanying drawings and the accompanying drawings include all modifications, equivalents or replacements included in technical spirits and technical scope of the present invention.

A mobile terminal has been enlarged to a type for performing various functions in association with various things including a smart phone that performs production and consuming functions of contents in addition to a communication function. Examples of the mobile terminal may include an object that may be worn by a user, that is, a wearable device such as a smart watch, smart glasses, a head mounted display (HMD), an eye mounted display (EMD), clothes, and shoes.

Hereinafter, in this specification, for understanding of the present invention and convenience of description, a wearable device will be described based on shoes, especially smart shoes. The smart shoes may provide various kinds of information such as the result of analysis for information on activity or movement of a wearer and recommended information related to the analysis result and a feedback for the information through a mobile terminal such as a smart phone and a smart watch. In this case, the smart shoes may perform sensing, tracing, analyzing, recording, and proposal functions of information on movement of a user who wears the smart shoes, for example, activity time, activity distance, and activity track. The information on movement of the wearer may be sensed using various sensors. Examples of the sensors may include any one or combination of two or more of a pressure sensor, an acceleration sensor, a global positioning system (GPS), a gyro sensor, a magnetic sensor, and a barometer sensor. In this case, although the sensors may mainly be included in an insole or midsole of the smart shoes, some sensors may be included in a device, which performs data communication with the smart shoes, such as a smart terminal. Hereinafter, in this specification, the sensor mainly means a pressure sensor or/and an acceleration sensor.

One example of the smart shoes according to one embodiment of the present invention comprises a communication unit for transmitting and receiving a signal to and from an external device, a sensor module for sensing first movement data of a user who wears the smart shoes through a first sensor, a memory for storing data sensed by the sensor module, and a controller for controlling turn-on/turn-off of a second sensor on the basis of the first movement data sensed through the first sensor included in the sensor module to sense second movement data of the user who wears the smart shoes.

A smart terminal service system comprises a smart terminal and smart shoes for performing data communication with the smart terminal, wherein the smart shoes includes a communication unit for transmitting and receiving a signal to and from the smart terminal, a sensor module for sensing first movement data of a user who wears the smart shoes through a first sensor, a memory for storing data sensed by the sensor module, and a controller for controlling turn-on/turn-off of a second sensor on the basis of the first movement data sensed through the first sensor included in the sensor module to sense second movement data of the user who wears the smart shoes and identifying the first movement data sensed through the first sensor with the second movement data sensed through the second sensor to transmit the identified result to the smart terminal, and the smart terminal configures a user interface on the basis of the first and second movement data transmitted from the smart shoes and outputs the configured user interface.

FIG. 1 is a view briefly illustrating a smart terminal service system that includes smart shoes according to one embodiment of the present invention.

Referring to FIG. 1, the smart terminal service system includes smarts shoes 110, a server 150, and one or more mobile terminals. At this time, the server 150 may not be required necessarily depending on a system.

The smart shoes 110 are implemented as a pair that includes one (hereinafter, 'left (L) smart shoe') of shoes for a left foot and one (hereinafter, 'right (R) smart shoe') of shoes for a right foot. At this time, a sensor module for smart shoes related to the present invention may be included in at least one of the left (L) smart shoe and the right (R) smart shoe. However, in this specification, for understanding of the present invention and convenience of description, the case that the sensor module for the smart shoes is included in both the left (L) smart shoe and the right (R) smart shoe will be described exemplarily.

The smart shoes 110 senses movement of a user, that is, a wearer who wears the smart shoes, and transmits movement information of the sensed user to one or more mobile terminals directly or indirectly through the server 150. In this case, a smart phone 120, a smart watch 130, etc. may be included in one or more mobile terminals. Also, the smart shoes 110 may also transmit the movement information to a digital TV 140, a digital signage (not shown), etc. However, it will be apparent that the smart shoes 110 may perform data communication with various devices in addition to the aforementioned terminals or shown device.

Meanwhile, the smart shoes 110 may perform data communication with terminals located at a short distance by using a short-range communication protocol or perform data communication with terminals located at a long distance by using the server 150. Alternatively, regardless of the distance, the smart shoes 110 may upload movement information of the user on the server 150 such as a cloud or conveniently download the movement information through the terminal at a desired place at any time.

In addition, the smart shoes 110 may perform data communication with at least two or more terminals simultaneously or sequentially.

Figure 2:
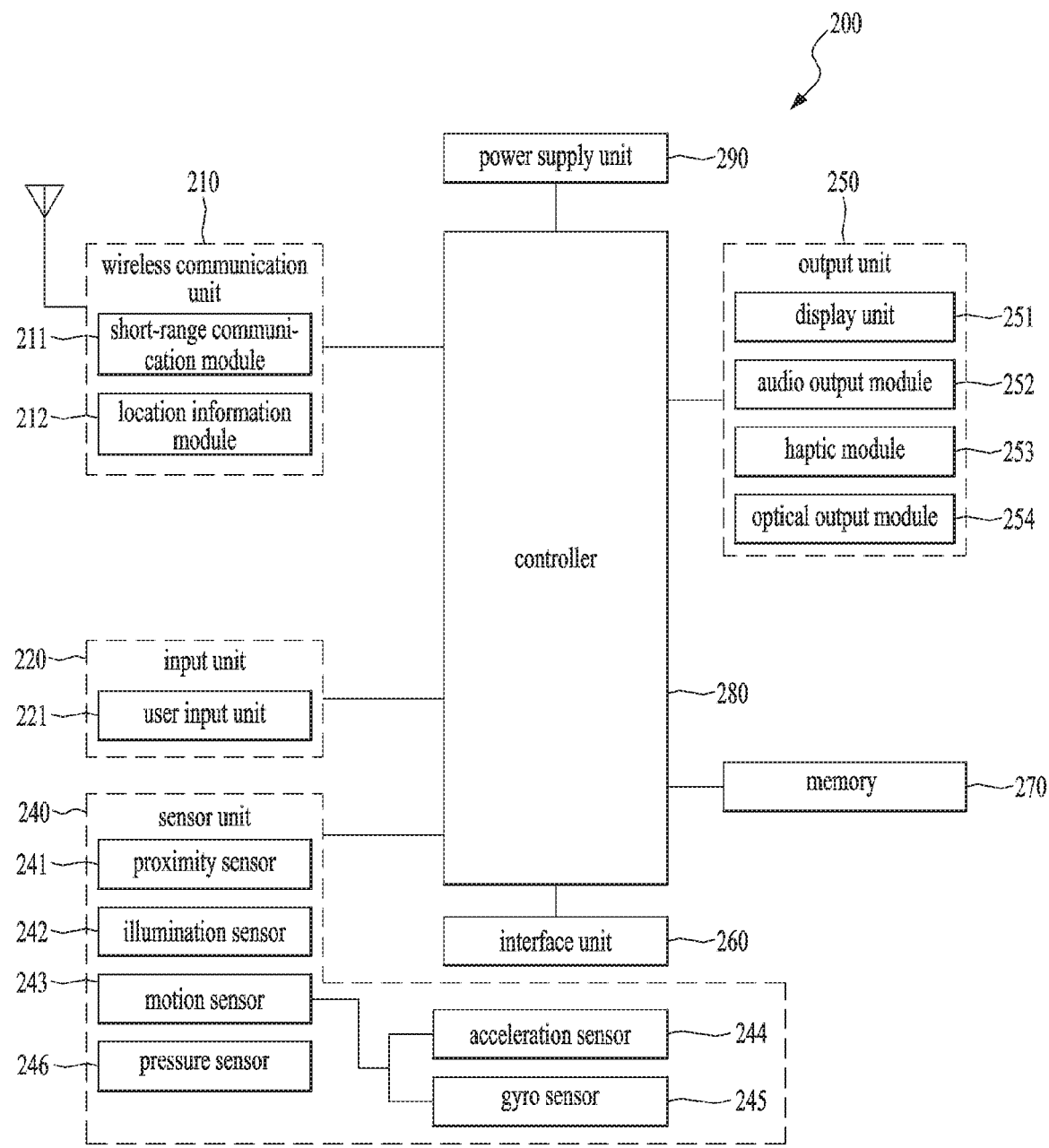
FIG. 2 is a block diagram illustrating a smart shoes sensor module 200 according to one embodiment of the present invention.

FIG. 2 is a block diagram illustrating a smart shoes sensor module 200 according to one embodiment of the present invention. In this case, a configuration of the smart shoes sensor module 200 will be described in FIG. 2 but its configuration may be regarded as a configuration of the mobile terminal. At this time, some components of the smart shoes sensor module 200 may be different from those shown.

The smart shoes sensor module 200 may include a wireless communication unit 210, an input unit 220, a sensor unit 240, an output unit 250, an interface unit 260, a memory 270, a controller 280, and a power supply unit 290. The components shown in FIG. 2 are not required necessarily for implementation of the smart shoes sensor module 200. The smart shoes sensor module 200 described in this specification may have components more than or smaller than the components listed above.

In more detail, the wireless communication unit 210 of the aforementioned components may include one or more modules that enable wireless communication between the smart shoes sensor module 200 and a wireless communication system, between the smart shoes sensor module 200 and another mobile terminal, or between the smart shoes sensor module 200 and an external server. Also, the wireless communication unit 210 may include one or more modules that connect the smart shoes sensor module 200 to one or more networks.

The wireless communication unit 210 may include at least one of a short-range communication module 211 and a location information module 212.

The short-range communication module 211 may be connected with the smart shoes module 200 through a Bluetooth mode and transmit and receive data to and from the smart shoes module 200.

The location information module 211 serves to measure or transmit location information of the smart shoes module 200, and may include a concept redundant with a motion sensor 243 which will be described later.

The input unit 220 may include a user input unit 221 (for example, touch key, push key (mechanical key), etc.) for receiving information from a user. Audio data or image data collected by the input unit 220 may be analyzed and processed as a control command of a user. The input unit 220 may serve to input an on/off function for enabling or disabling a function of the smart shoes module 200, or may be omitted for saving of the production cost or lightweight if necessary.

The sensor unit 240 may include one or more sensors for sensing at least one of information in the smart shoes module 20, peripheral environment information surrounding the smart shoes module 200 and user information. For example, the sensor unit 240 may include at least one of a proximity sensor 241, an illumination sensor 242, a touch sensor, an acceleration sensor 244, a magnetic sensor, a gravity sensor (G-sensor), a gyroscope sensor 245 (hereinafter, 'gyro sensor'), a motion sensor 243, an RGB sensor, an infrared (IR) sensor, a finger scan sensor, an ultrasonic sensor, an optical sensor, a battery gauge, an environment sensor (for example, a barometer, a hygrometer, a thermometer, a radiation detection sensor, a thermal sensor, and a gas sensor), and a chemical sensor (for example, an electronic nose, a health care sensor, a biometric sensor, and the like). Meanwhile, the smart shoes module 200 disclosed in this specification may be configured to utilize information obtained from one or more sensors of the sensor unit 240 and combinations thereof.

Particularly, the acceleration sensor 244 and the gyro sensor 345, which are mentioned in the present invention, may be included in the motion sensor 243.

The motion sensor 243 packaged in the smart shoes sensor module 200 may mean a component for directly sensing movement of the smart shoes sensor module 200. The motion sensor 243 may include the acceleration sensor 244 and the gyro sensor 245. If necessary, the motion sensor 243 may include any one of the acceleration sensor 244 and the gyro sensor 245.

Movement such as location change relative to two-dimensional or three-dimensional location and time of the smart shoes sensor module 200 may be sensed through the motion sensor 243.

The motion sensor 243 and the controller 280 may be included in the smart shoes sensor module 200 or may be packaged in the smart shoes 110 as a separate component.

The pressure sensor 246 is packaged in the smart shoes sensor module 200 and senses a pressure. The pressure sensor 246 may functionally be included in the motion sensor 243. In the present invention, the motion sensor 243 includes the acceleration sensor 244 and the gyro sensor 245, and the pressure sensor 246 will be described as a separate component independent from the motion sensor 243.

The output unit 250 is configured to output various types of information, such as audio, video, tactile output, and the like. The output unit 250 may include at least one of a display unit 251, an audio output module 252, a haptic module 253, and an optical output module 24.

The interface unit 260 serves as an interface with various types of external devices that can be coupled to the smart shoes sensor module 200. The interface unit 260, for example, may include at least one of external power supply ports, wired or wireless data ports, memory card ports, and ports for connecting a device having an identification module. The smart shoes sensor module 200 may perform assorted control functions associated with a connected external device, in response to the external device being connected to the interface unit 260.

Also, the memory 270 is implemented to store data to support various functions or features of the smart shoes sensor module 200. The memory 270 may be configured to store data or instructions for operations of the controller driven in the smart shoes sensor module 200.

The controller 280 typically functions to control an overall operation of the smart shoes sensor module 200, in addition to the operations associated with an application. The controller 280 may process signals, data, information and the like inputted or outputted through the above-mentioned components and/or runs the data or instructions stored in the memory 170, thereby processing or providing a user with appropriate information and/or functions.

The power supply unit 290 can be configured to receive external power or provide internal power in order to supply appropriate power required for operating elements and components included in the smart shoes sensor module 200. The power supply unit 290 may include a battery, and the battery may be configured to be embedded in the smart shoes sensor module, or configured to be detachable from the smart shoes sensor module.

At least one portion of the respective components mentioned in the foregoing description can cooperatively operate to embody operations, controls or controlling methods of the smart shoes sensor module 200 according to various embodiments of the present invention mentioned in the following description. Moreover, the operations, controls or controlling methods of the smart shoes sensor module 200 can be embodied in the smart shoes sensor module 200 by running at least one or more data or instructions stored in the memory 170.

Figure 3:
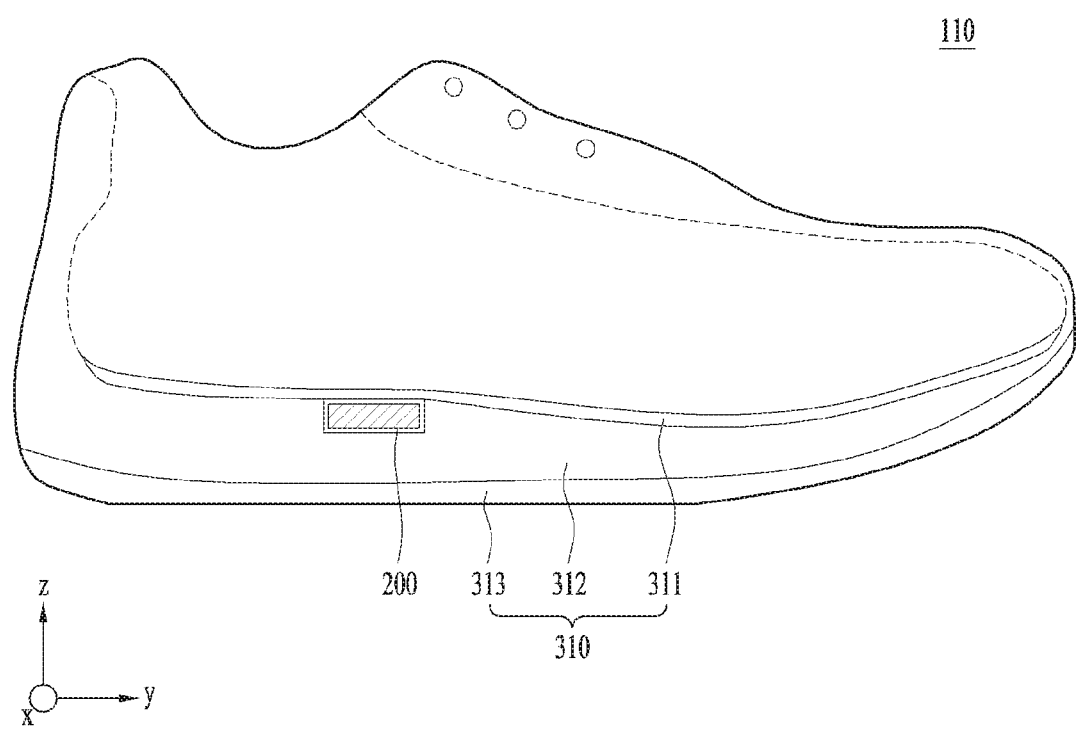
FIG. 3 is a cross-sectional view of a y-z plane of smart shoes 110 provided with a smart shoes sensor module 200 according to one embodiment of the present invention.

FIG. 3 is a cross-sectional view of a y-z plane of smart shoes 110 provided with a smart shoes sensor module 200 according to one embodiment of the present invention.

A sole frame 310 of the smart shoes 110 means a direct/indirect area in which the soles of the wearer are in contact. In other words, the sole frame 310 may mean a frame of an area provided between a foot and sole of the wearer in the smart shoes sensor module 200. The sole frame 310 may include an insole 311 in which the sole of the wearer is directly in contact, an outsole 313 provided on the lowest end of the smart shoes sensor module 200, being directly in contact with the outside, that is, ground, and a midsole 312 provided between the insole 311 and the outsole 313, forming a certain volume.

The insole 311 may be a shoe insert which is commonly mentioned, but may be configured in a single body with the midsole 312 without distinction of the insole 311 and the midsole 312, if necessary, or may be provided in a coupled type with the midsole 312 by an adhesive although provided as a separate member.

The smart shoes sensor module 200 may be provided on the sole frame 310. The smart shoes sensor module 200 may process the sole frame 310 as signal or data in accordance with a pressure applied by walking or driving of the wearer.

Figure 4:
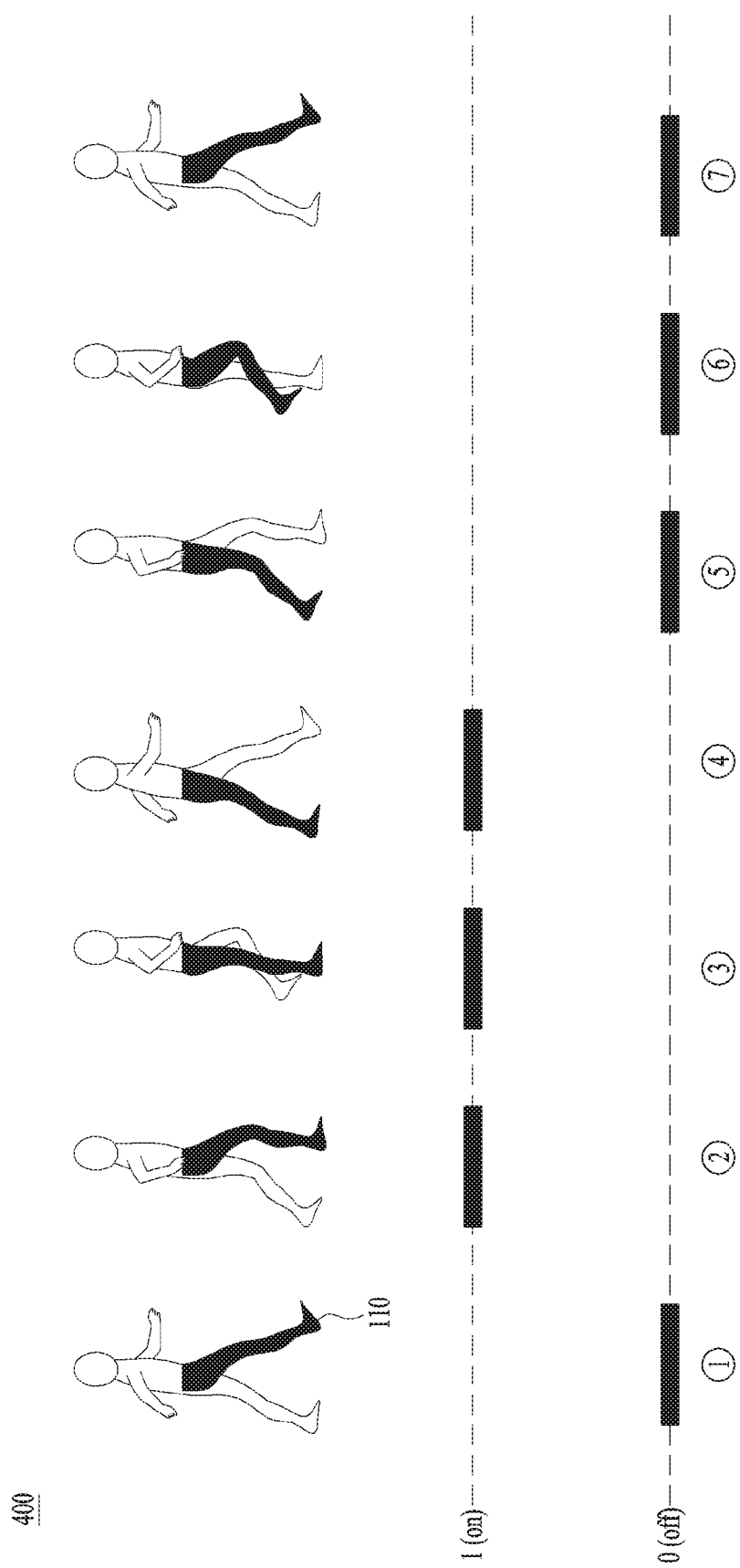
FIG. 4 is a view illustrating time sequential correspondence to walking of a smart shoes wearer 400 provided with a smart shoes sensor module 200 according to one embodiment of the present invention and a signal generated in accordance with walking.

FIG. 4 is a view illustrating time sequential correspondence to walking of a smart shoes wearer 400 provided with a smart shoes sensor module 200 according to one embodiment of the present invention and a signal generated in accordance with walking.

An on signal '1' may be generated in the smart shoes sensor module 200 when the wearer 400 who wears the smart shoes 110 steps on the ground, whereas an off signal '0' may be generated in the smart shoes sensor module 200 when the wearer 400 does not step on the ground.

A value of '1', that is, the on signal may be generated in the smart shoes sensor module 200 as a pressure value of a specific value or more acts on states ②to ④ of FIG. 4, and a value of '0', that is, the off signal may be generated in the smart shoes sensor module 200 as a pressure value less than a specific value acts on the other states ① and ⑤-⑦.

The on signal generated in the smart shoes sensor module 200 may be generated by a predetermined threshold pressure value.

The predetermined threshold pressure value may be determined in accordance with material rigidity and elasticity of the smart shoes sensor module 200, a size of the smart shoes sensor module 200, or an interval between a conductive member and a first circuit.

For example, if the predetermined threshold pressure value is more increased, a pressure threshold value that may generate the on signal is more increased. Therefore, the value of '1', that is, the on signal may be generated in the smart shoes sensor module 200 in case of the states ② and ③, and the value of '0', that is, the off signal may be generated in the smart shoes sensor module 200 in case of the other states ① and ④-⑦.

Therefore, through this result, start and end of one step of the wearer may be determined, and if the step is repeated, a cycle of each step may be identified.

Referring to FIG. 4, ② may be construed as a start of one step and a point of ① after passing through ⑦ may be construed as an end of one step.

Also, if a change from ② to ① is repeated, a plurality of steps may be construed by identifying one cycle as one step.

In the case that a unit of a step is construed using the acceleration sensor 244 (see FIG. 2) and/or the gyro sensor 245 (see FIG. 2) of the motion sensor 243 (see FIG. 2), an error may occur due to various factors, that is, noise in case of a point where a velocity value of the smart shoes sensor module 200 is '0'. However, in the present invention, the noise may be removed through the on/off signal based on the pressure sensor in the smart shoes sensor module 200, whereby an exact step unit may be identified.

The smart shoes sensor module 200 may be operated depending on whether a pressure acts on a direction toward the sole frame 310 (see FIG. 3) from the sole of a foot, that is, a lower direction. However, the lower direction is not required necessarily, and the smart shoes sensor module 200 may be operated based on a pressure for a direction dislocated at a certain angle with respect to the lower direction if necessary. If a plurality of smart shoes sensor modules 200 are provided, they may be operated with respect to various directions.

The direction of the pressure may be based on a normal step and power action of the wearer, or may be varied depending on a step and power action of another wearer.

The predetermined threshold pressure value may be applied differently depending on physical habitual factors of the wearer, such as height, weight, foot size, sex, and age. However, since on/off of the smart shoes sensor module 200 may depend on material and structure, the smart shoes sensor module 200 of which material and structure are determined may have a predetermined threshold pressure value. This threshold pressure value may be changed randomly considering sensing data exactness for the wearer, noise, etc.

Figure 5:
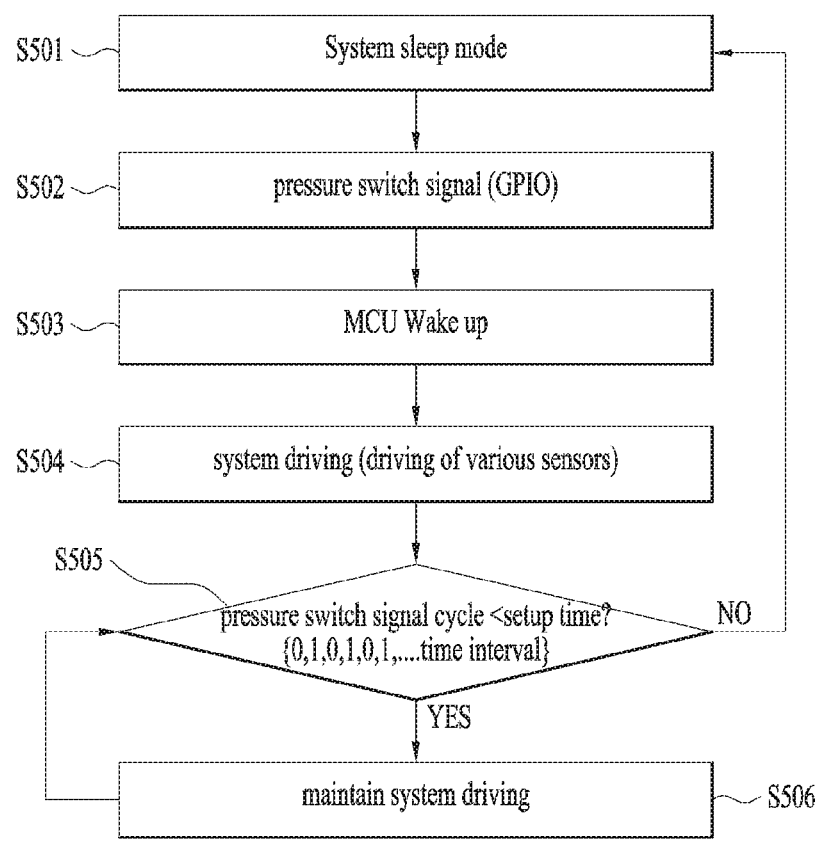
FIG. 5 is a flow chart illustrating an operation of a smart shoes sensor module 200 according to one embodiment of the present invention.

FIG. 5 is a flow chart illustrating an operation of a smart shoes sensor module 200 according to one embodiment of the present invention.

The controller 280 may perform current supply and control of the motion sensor 243 on the basis of the on or off signal of the smart shoes sensor module 200.

If the off signal of the smart shoes sensor module 200 is generated continuously for a certain time or more, it may be construed that the user has not worn the smart shoes 110 or does not move even though the user has worn the smart shoes 110. Alternatively, it may be construed that the user has not performed movement that generates the predetermined threshold pressure or more even though the user has worn the smart shoes 110. For example, this case may include a case that the user who wears the smart shoes 110 sits on a chair and moves slightly even though the user steps on the ground or not.

Therefore, the controller 280 may perform a system sleep mode for minimizing a power consumed for the smart shoes sensor module 200 by disabling the motion sensor 243 (S501).

If the on signal is generated in the smart shoes sensor module 200 during the system sleep mode, it may be construed that the user performs activity while wearing the smart shoes 110 (S502).

Therefore, the one signal of the smart shoes sensor module 200, which is generated during the system sleep mode, may enable the controller 280 (S503). If the controller 280 is already enabled, this step may be omitted.

The controller 280 may release the system sleep mode of the smart shoes sensor module 200 and drive the system (S504). In this case, driving of the system may mean that various electronic parts, circuits and sensors provided in the smart shoes sensor module 200 are turned on.

The controller 280 compares a time interval of occurrence of the on and off signals of the smart shoes sensor module 200 with a predetermined time interval in real time (S505).

If the time interval of occurrence of the on and off signals of the smart shoes sensor module 200 is within the predetermined time interval, that is, if the value of 1 of the on signal is received within a predetermined time, system driving of the smart shoes sensor module 200 may be maintained (S506).

On the other hand, if the time interval of occurrence of the on and off signals of the smart shoes sensor module 200 exceeds the predetermined time interval, that is, if the value of '0' of the off signal is received continuously for a predetermined time or more, the controller 280 may disable the overall system of the smart shoes sensor module 200. That is, the controller 280 may switch system driving to the system sleep mode. In this case, the controller 280 may perform current breaking and deactivation for the motion sensor 243.

Figure 6:
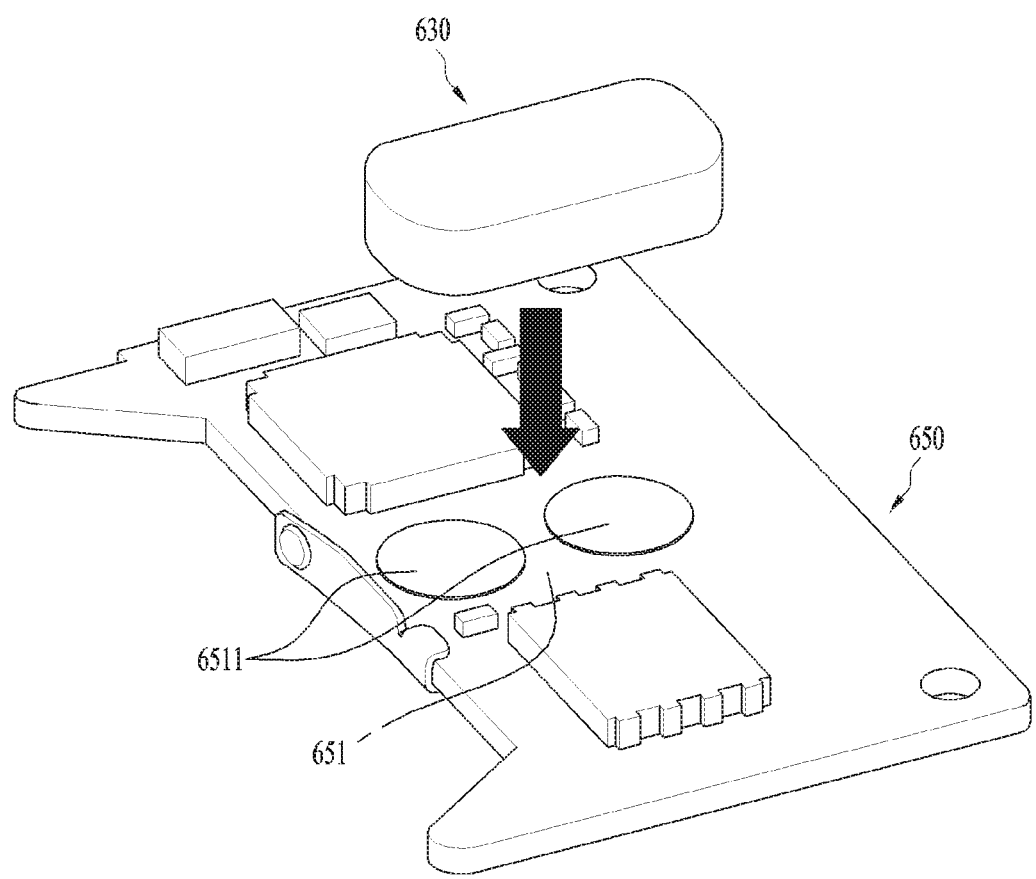
FIG. 6 is a view illustrating a system or circuit configuration of a smart shoes sensor module 200 according to one embodiment of the present invention.

FIG. 6 is a view illustrating a system or circuit configuration of a smart shoes sensor module 200 according to one embodiment of the present invention.

A pressure conductive member 630 according to the present invention, which is one of core components of the smart shoes sensor module 200 may be operated in association with a first circuit 651. The first circuit 651 may be packaged on a substrate 650 and then at least one area of the first circuit 651 may be exposed on the substrate 650.

In this case, for convenience, FIG. 6 illustrates a state before coupling between the conductive member 630 and the first circuit 651, wherein the conductive member 630 may be fixed to the substrate 650 by being spaced apart from the substrate 650 by another member, or may be fixed to the substrate 650 in contact with the substrate 650.

If a pressure less than a threshold value acts on the smart shoes sensor module 200, the conductive member 630 is electrically detached from the first circuit 651.

The first circuit 651 may maintain an open circuit, that is, an electrically open state until the first circuit 651 is connected to the conductive member 630.

If a pressure more than a threshold value acts on the smart shoes sensor module 200, the conductive member 630 may electrically be connected with contact terminals 6511 of the first circuit 651.

The two contact terminals 6511 which are spaced apart from each other may electrically be connected with each other by the conductive member 630, whereby the first circuit 651 may maintain a closed circuit. If the first circuit 651 configures a closed circuit, an electric signal may be generated.

The controller 280 may recognize the electric signal generated in the first circuit 651 as the aforementioned on/off signal of FIG. 5, and may control various operations on the basis of the recognized on/off signal.

Since the controller 280 recognizes the electric signal generated as the on/off signal, although the recognized operation may be construed as a separate independent procedure, it may be construed as one operation performed by one circuit.

Meanwhile, as one embodiment, although two contact terminals 6511 related to electric connection and connection release between the pressure conductive member 630 and the first circuit 651 are shown in FIG. 6, the present invention is not limited to the example of FIG. 6. For example, at least one or more contact terminals 6511 may be provided. Also, although not shown, electric connection and connection release between the pressure conductive member 630 and the first circuit 651 may be implemented in a non-contact mode instead of a contact mode based on the contact terminals 6511.

FIG. 7 is a view illustrating an example of an external appearance of a smart shoes sensor module 200 including a circuit configuration of FIG. 6.

FIG. 7a is a front perspective view illustrating an external appearance of the smart shoes sensor module 200, and FIG. 7b is a rear perspective view illustrating an external appearance of the smart shoes sensor module 200.

A housing 760 constituting the external appearance of the smart shoes sensor module 200 may include an upper case 761 and a lower case 762. Although the upper case 761 and the lower case 762 may be formed in a uni-body type. 300, the upper case 761 and the lower case 762 may be formed respectively in a separate body and then coupled to each other in the present invention.

Also, in this specification, although the smart shoes sensor module 200 is formed by coupling between two cases, that is, the upper case 761 and the lower case 762, the present invention is not limited to this case, and the smart shoes sensor module 200 may be formed by coupling between two or more cases as the case may be.

Figure 8:
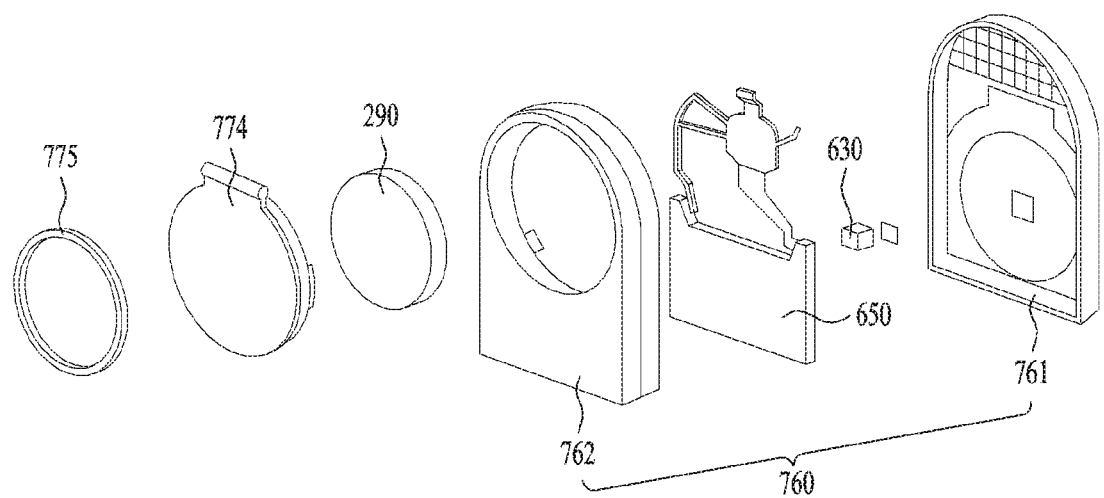
FIG. 8 is a view illustrating an individual configuration of a smart shoes sensor module 200 according to one embodiment of the present invention.

FIG. 8 is a view illustrating an individual configuration of a smart shoes sensor module 200 according to one embodiment of the present invention.

The smart shoes sensor module 200 may mean a structural unit for packaging components that perform functions of the pressure sensor 246 (see FIG. 2), and may physically include all the components packaged in the housing 760.

The housing 760 may package the components such as the substrate 650. The housing 760 may be configured by coupling between the upper case 761 and the lower case 762, which are provided on a front surface thereof.

The power supply unit 290 may be packaged in the housing 760 to serve to supply a power to the controller 280, etc. For active exchange of the power supply unit 290, the power supply unit 290 may include a battery cover 774 coupled to the lower case 762. A gap between the battery cover 774 and the lower case 762 may be stopped by a waterproof ring 775, whereby no problem may occur in waterproof.

Figure 9:
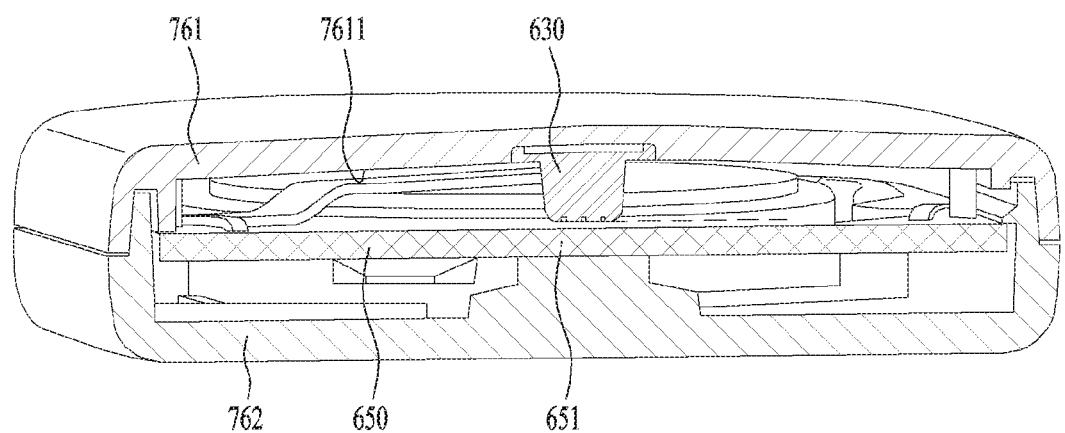
FIG. 9 is a cross-sectional view taken along line A-A' of FIG. 7.

FIG. 9 is a cross-sectional view taken along line A-A' of FIG. 7.

The upper case 761 may form an upper appearance of the smart shoes sensor module 200, and may elastically move by means of a pressure of a threshold value or more which acts on a first direction. The first direction may mean a ground direction from feet of the wearer. In other words, the first direction may mean a direction from the upper case 761 to the lower case 762.

The upper case 761 may be formed in a thin plane shape to transfer a pressure from the sole of the wearer to the conductive member 630, and may be provided to directly adjoin the conductive member 630. An outer surface of the upper case 761 is formed to be convex, whereby a pressure from feet of the wearer or a pressure from a shoe insert, which is transferred from the feet of the wearer, may be well transferred to the upper case 761. The upper case 761 may include an elastic material if necessary to well transfer the pressure to the conductive member 630. For example, the upper case 761 may be formed of a silicon material.

The lower case 762 may be coupled to the lower end of the upper case 761 to form a lower appearance of the smart shoes sensor module 200.

The first circuit 651 may be provided by being packaged in the housing 760 in which the upper case 761 and the lower case 762 are formed, and especially may be fixed to the lower case 762.

The first circuit 651 may partially be exposed from one surface on the substrate 650 and then may be in contact with the conductive member 630 which will be described later.

The first circuit 651 may be implemented as a coupling type of a film and a metal electrode or may be implemented as a coupling type of a film and a conductive polymer. Or, the first circuit 651 may be implemented in a type of a film and CNT or a type of a film and Graphene.

Or, the first circuit 651 may be provided in a type of a molding material and MID (Mold Interconnect Devices).

The substrate 650 may package the first circuit 651. The substrate 650 may package a second circuit for driving the motion sensor 243. The substrate 650 may package the controller 280. However, it is not required that the motion sensor 243, the second circuit or the controller 280 should be provided in the smart shoes sensor module 200. The smart shoes 110 may include the motion sensor, 243, the second circuit or the controller 280, which is separately provided, in accordance with the need or the system.

The conductive member 630 may generate an electric signal in the first circuit 651.

The conductive member 630 may be packaged in the housing 760 in which the upper case 761 and the lower case 762 are formed, and especially may be provided at an inner side of the upper case 761.

The conductive member 630 may be provided at the inner side 7611 of the upper case to form a first gap with the first circuit 651, and may elastically move by means a pressure of a threshold value or more which acts on the upper case 761 in a first direction, whereby the conductive member 630 may be in contact with the first circuit 651 and may generate a signal.

That is, the conductive member 630 may perform the function of the pressure sensor 246 (see FIG. 2) in accordance with the pressure of a threshold value or more, which acts on the upper case 761, in contact with the first circuit 651. If the pressure of a threshold value or more acts on the smart shoes sensor module 200, an electric signal may be generated in the first circuit 651.

The conductive member 630 may serve to electrically connect the first circuit 651 when it is in contact with the first circuit 651. The conductive member 630 may include a conductive material. Therefore, the conductive member 630 may be implemented as a conductive silicone, metal gasket, metal plate material or metal deposition, conductive polymer, CNT, Graphene, etc.

Or, the first circuit 651 may be configured by combination of a molding material and MID (Mold Interconnect Device).

For convenience of description, the state that no pressure acts on the smart shoes sensor module 200 will be referred to as a first state, and the state that a pressure acts on the smart shoes sensor module 200 will be referred to as a second state.

At the first state, the conductive member and the first circuit 651 may form a first gap G1. The first gap G1 may be a specific value that exceeds 0 mm.

At the first state, the first gap G1 may be maintained, and at the second state, the conductive member 630 and the first circuit 651 may be in contact with each other by elastic movement of the upper case 761.

When the smart shoes sensor module 200 is formed, the first gap G1 may be varied depending on manufacturing tolerance of the upper and lower cases 761 and 762, manufacturing tolerance and coupling tolerance of the conductive member 630 and the substrate 650 provided with the first circuit 651, coupling tolerance of the conductive member 630 and the upper case 761, and coupling tolerance between the upper case 761 and the lower case 762.

If the first gap G1 does not have a fixed value, a threshold pressure value of signal occurrence is varied, whereby a boundary of the on signal and the off signal may be formed.

If a step generated due to offset in identification of the on signal and the off signal is not recognized, or if it is recognized that a step is generated although the step is not generated, a problem may occur in that an error is generated in analysis of a step pattern of the wearer and an accumulated error is generated to cause a different result.

Therefore, at the first state, the first gap G1 is maintained, that is, the conductive member 630 and the first circuit 651 are in contact with each other so as not to generate the on signal, whereby reliability may be maintained.

The upper case 761 and the lower case 762 may be coupled to each other as a pair of a coupling groove and a coupling protrusion.

The coupling groove and the coupling protrusion may be fixed to each other by a fitting manner, and may prevent the upper case 761 and the lower case 762 from being opened unintentionally.

The coupling groove may be provided at one side of the upper case 761 or the lower case 762, and the coupling protrusion may be provided at the other side.

The coupling groove and the coupling protrusion may be in contact with each other at their respective sides to exert a fitting effect.

The coupling groove and the coupling protrusion may form a second gap G2 with respect to a longitudinal direction. The second gap G2 may prevent a width of the first gap G1 from being varied due to tolerance generated between the coupling groove and the coupling protrusion.

Similarly, a third gap G3 may be formed at an outer boundary between the upper case 761 and the lower case 762.

A support rib may be protruded from the inner side of the upper case 761 toward a downward direction to support the substrate 651 that includes the first circuit 651. If the first circuit 651 is packaged in the lower case 762, the support rib may serve to allow the substrate 651, which includes the first circuit 651, not to move, thereby minimizing tolerance generated in the first gap G1 due to a space.

A hook portion may be provided to be protruded at the inner side of the lower case 762 and fix the substrate 650 that includes the first circuit 651.

The conductive member 730 may be coupled to the inner side 7611 of the upper case 761. In this case, the conductive member 730 may be coupled to the inner side 7611 of the upper case 761 through an adhesive tape, or may be coupled to the inner side 7611 of the upper case 761 simultaneously with the formation of the upper case 761 or at another time different from the formation of the upper case 761 by a double injection molding.

If the conductive member 730 is coupled to the inner side 7611 of the upper case 761, the conductive member 630 may be provided in a recess area of the upper case 761 to improve reliability of the coupling. The recess area may increase a contact area between the conductive member 630 and the inner side 7611 of the upper case, and may serve to assure a space to allow the conductive member 630 to have a predetermined thickness or more.

Figure 10:
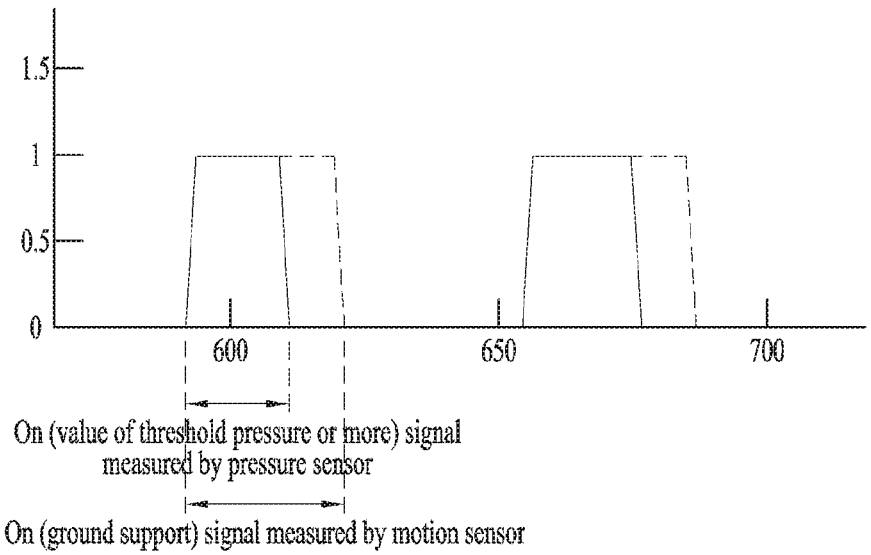
FIG. 10 is a view illustrating time difference between an on-signal measured by a motion sensor 243 of smart shoes 100 and an on-signal measured by a pressure sensor 246 in accordance with one embodiment of the present invention.

FIG. 10 is a view illustrating time difference between an on-signal measured by a motion sensor 243 of smart shoes 100 and an on-signal measured by a pressure sensor 246 in accordance with one embodiment of the present invention.

The motion sensor 243 may identify a three-dimensional location of the smart shoes 110 through the acceleration sensor 244 and the gyro sensor 245 in real time.

As a result, the controller 280 may identify and analyze whether the smart shoes sensor module 200 is an on signal state supported on the ground, that is, a value of '1' or an off signal state far away from the ground, that is, a value of '0'.

Meanwhile, the pressure sensor 246 may analyze the on signal state estimated to be supported on the ground or the off signal state estimated to be far away from the ground depending on the threshold pressure value or more for signal occurrence.

However, if the on signal or the off signal is determined through the pressure sensor 246, an error may occur due to manufacturing tolerance or coupling tolerance of the smart shoes sensor module 200.

Therefore, it is required that the state of the on signal or off signal, which is measured and analyzed through the pressure sensor 246 should be corrected to the on signal or off signal state measured or analyzed through the motion sensor 243, or vice versa.

Figure 11:
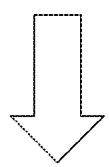
FIGS. 11 and 12 are algorithm and flow chart illustrating that a smart shoes on-signal value measured through a pressure sensor 246 is calibrated to a smart shoes on-signal value measured through a motion sensor 243 in accordance with one embodiment of the present invention.
Figure 12:
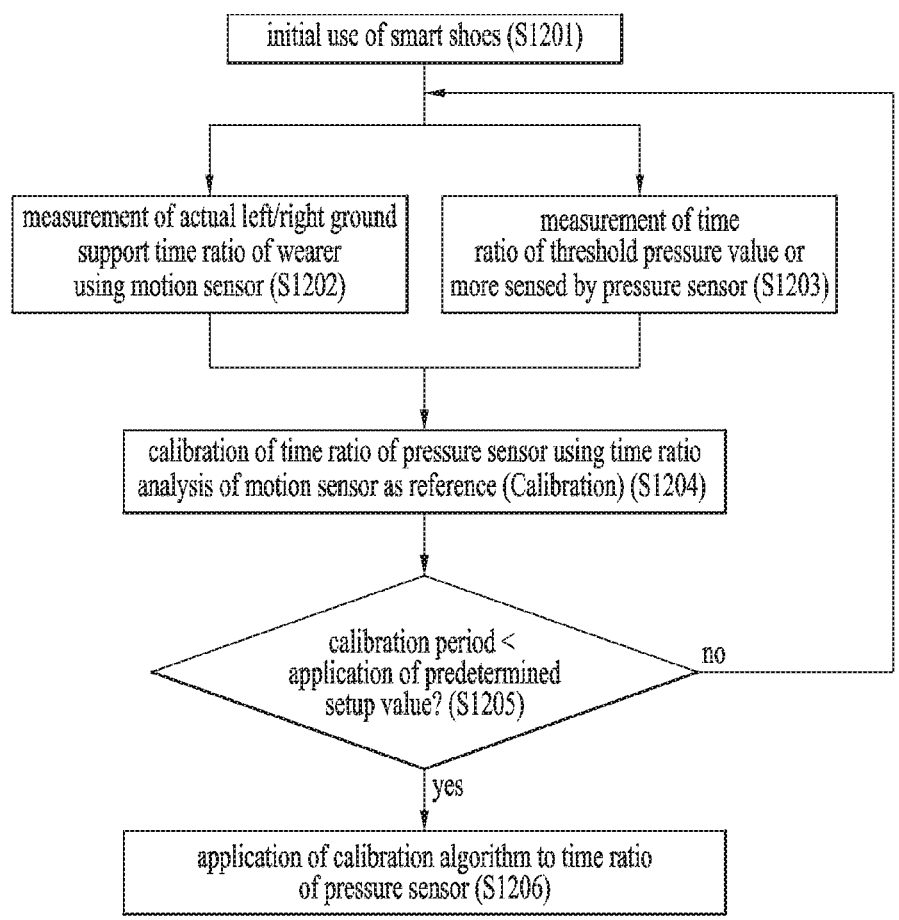

FIGS. 11 and 12 are algorithm and flow chart illustrating that a smart shoes on-signal value measured through a pressure sensor 246 is calibrated to a smart shoes on-signal value measured through a motion sensor 243 in accordance with one embodiment of the present invention.

The smart shoes sensor module 200 may be provided at each of a left (L) smart shoe and a right (R) smart shoe to analyze a step pattern of the wearer.

The smart shoes sensor module 200 provided at the left (L) smart shoe will be defined as a left (L) smart shoe sensor module, and the smart shoes sensor module 200 provided at the right (R) smart shoe will be defined as a right (R) smart shoe sensor module. A unit of organically measure and analyze the left (L) smart shoe sensor module and the right (R) smart shoe sensor module is defined as a smart shoes sensor module system.

That is, a measured value or analyzed value of any one of the left (L) smart shoe sensor module and the right (R) smart shoe sensor module may be transmitted to the smart shoe sensor module of the other side, or a separate mobile terminal may perform correction by receiving the measured value and analyzed value of each smart shoe sensor module.

In the former case, the left (L) smart shoe sensor module and the right (R) smart shoe sensor module may be regarded as the smart shoes sensor module system. In the latter case, the left (L) smart shoe sensor module, the right (R) smart shoe sensor module and the separate mobile terminal may be regarded as the smart shoes sensor module system.

The aforementioned error between the pressure sensor 246 and the motion sensor 243 in FIG. 10 may be enlarged to a problem of an on signal time of the left smart shoe and the right smart shoe.

The time supported on the ground depending on the step pattern of the wearer, that is, the time or ratio that a pressure of a threshold value or more is applied may differently be applied to the left (L) smart shoe and the right (R) smart shoe. Therefore, this difference may cause an inexact result during analysis of the step pattern of the wearer. It is therefore required to correct such a difference in balance.

A difference in left and right sides for analysis of the time of the left and right (L/R) smart shoes sensor module 200 supported on the ground may occur due to complex factors such as a difference caused by imbalance between left and right weights of the wearer as well as a factor caused by manufacturing tolerance of each of the left/right (L/R) smart shoes sensor modules 200.

Therefore, it is required to calibrate time difference of the left/right (L/R) smart shoes supported on the ground, which is measured by the pressure sensor 246.

Such calibration may be performed through support time analysis of the motion sensor 243 supported on the ground, wherein the motion sensor 243 is provided at each of the left/right (L/R) smart shoes.

The motion sensor 243 may measure three-dimensional locations of the left/right (L/R) smart shoes 110 through the acceleration sensor 244 and the gyro sensor 245 in real time, as described above.

The motion sensor 243 may analyze a start point and an end point of the smart shoes 110 supported on the ground on the basis of the measured locations.

The difference in the on signal time ratio of the left/right smart shoes 110, which is identified through the pressure sensor 246, may be calibrated based on the ratio of the support time of each of the left/right (L/R) smart shoes supported on the ground, which is analyzed through the motion sensor 243.

For example, if the smart shoes 110 are initially used, a calibration algorithm may be actuated automatically (S1201).

The controller 280 may analyze the ground support time ratio through three-dimensional movement of the left/right (L/R) smart shoes 110, which is measured by the motion sensor 243 that includes the acceleration sensor 244 and the gyro sensor 245 (S1202), and may analyze the time ratio acted on the left/right smart shoes 110 at a threshold pressure value or more, which is measured by the pressure sensor 246 (S1203).

The measuring or analyzing steps may be performed at the same time or different times.

For example, it is assumed that the ground support time ratio measured and analyzed through the motion sensor 243 is 0.8:1.2, and the time ratio acted on the left/right smart shoes 110 at a signal occurrence threshold pressure value or more, which is measured and analyzed through the pressure sensor 246, is 0.9:1.1.

In this case, the controller 280 may apply a calibration algorithm that multiplies 0.8/0.9 by the value measured by the pressure sensor 246 of the left (L) smart shoe and multiples 1.2/1.1 by the value measured by the pressure sensor 246 of the right (R) smart shoe (S1204, S1206).

However, in order to minimize power consumption, the controller 280 may drive the motion sensor 243 at only the initial correction step of the pressure sensor 246 and disable driving of the motion sensor 243 if it is not necessary.

That is, the controller 280 may temporarily enable the motion sensor 243, which is disabled, when performing calibration.

Calibration of the controller 280 may be performed by a cycle set by the wearer, or may be performed automatically at a predetermined cycle (S1205).

The smart shoes system according to the present invention has been described with reference to FIGS. 1 to 12. Hereinafter, a smart shoes tracing algorithm based on sensing data of the pressure sensor in a PDR (Pedestrian Dead Reckoning) algorithm, will be described in detail.

Hereinafter, the smart shoes system operated based on the smart shoes tracing algorithm will be described in more detail.

In this case, the smart shoes tracing algorithm may refer to sensing data of the pressure sensor in the PDR algorithm to exactly sense movement (for example, every step) of the smart shoes wearer without missing the movement. If the smart shoes tracing algorithm is used, movement data such as step track, step direction, stride and height of the smart shoes wearer may be calculated more easily and exactly. Moreover, if the smart shoes tracing algorithm is used, power consumption may be minimized and efficiency may be maximized as compared with the smart shoes system of the related art, in association with the aforementioned pressure switch or pressure sensor circuit or module.

The smart shoes according to the present invention may perform tracing, sensing and recording of movement data such as moving time, velocity, distance or position, orientation, trace or path, altitude and stride in a state that the user wears the smart shoes. At this time, it is important to exactly perform tracing and sensing without missing every step of the smart shoes wearer.

In respect of the present invention, in sensing movement data of the smart shoes wearer, if movement data of the wearer is measured using only the motion sensor (or referred to as PDR sensor or inertia sensor) such as the acceleration sensor and the gyro sensor, the motion sensor should always maintain a measurable state. However, enabling of the motion sensor causes continuous battery consumption. Also, when the movement data is sensed using the motion sensor, a step of the wearer may not be identified exactly due to noise generated in the motion sensor, for example, an error such as missing of one step may occur. If this error is accumulated, an error occurs in the movement data of the wearer, which is acquired through sensing, whereby reliability is reduced. To solve this problem, the motion sensor of the present invention further includes a pressure switch or pressure sensor as described above. The pressure switch or pressure sensor will be described based on the aforementioned description, and its repeated description will be omitted.

Hereinafter, the smart shoes tracing algorithm, movement data sensing through the smart shoes tracing algorithm, and the smart shoes system for the movement data sensing will be described in more detail.

Figure 13:
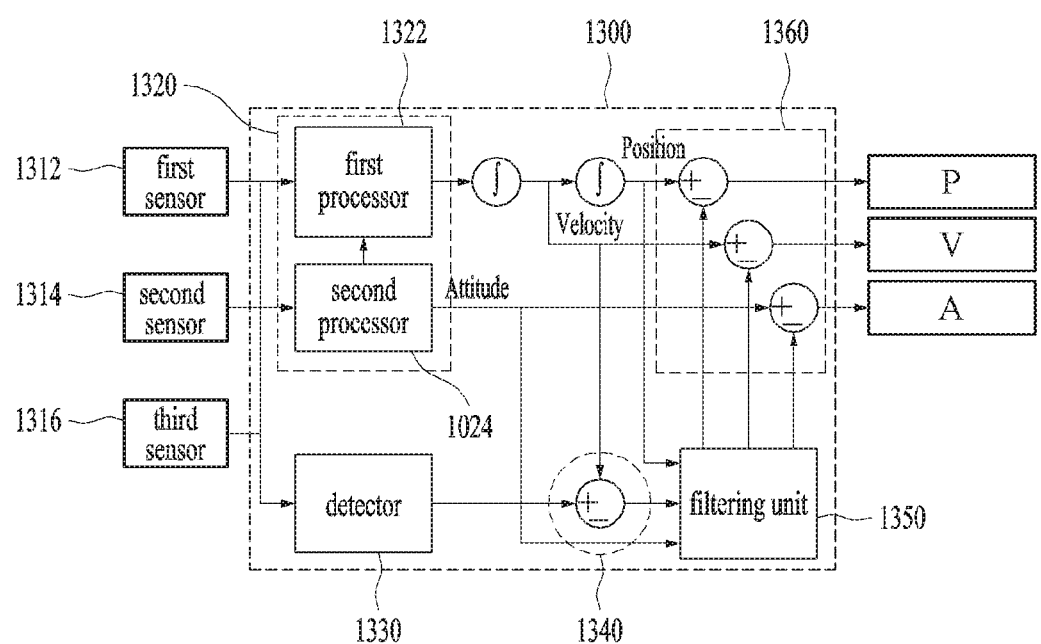
FIG. 13 is a schematic block diagram illustrating a tracing algorithm in a smart shoes system according to one embodiment of the present invention.

FIG. 13 is a schematic block diagram illustrating a tracing algorithm in a smart shoes system according to one embodiment of the present invention.

Referring to FIG. 13, the smart shoes tracing algorithm may be processed by a component called a smart shoes tracing data processor 1300 (hereinafter, referred to as 'tracing data processor'). The scope of the tracing data processor 1300 should be determined with reference to its function or role. The tracing data processor 1300 may be implemented by hardware such as circuit or module or embedded software embedded in one component of the aforementioned smarts shoes system. However, it is not required that the tracing data processor 1300 disclosed in FIG. 13 and this specification should be one component of the smart shoes. The tracing data processor 1300 may be designed as one component included in another device (including server) such as a mobile terminal that may receive and process sensing data of the sensors of the smart shoes.

The tracing data processor 1300 may accumulate and calculate a moving distance (position (3D)) by estimating a moving velocity (3D)) and a moving direction (attitude (3D)) of the smart shoes wearer through a sensor module mounted in the smart shoes.

The tracing data processor 1300 may process tracing data for the smart shoes wearer by using a processor 1320 and a filtering unit 1350 on the basis of sensing data of the sensor module mounted in the smart shoes. This is related to a PDR algorithm related to an inertia navigation system of the related art, and its detailed description will be based on the PDR algorithm of the related art. In this case, the detailed description of the PDR algorithm will be omitted.

First of all, a procedure of processing tracing data through the processor 1320 and the filtering unit 1350 will be described.

The processor 1320 includes a first processor 1322 and a second processor 1324.

The first processor 1322 receives data sensed by a first sensor 1312, processes the received sensing data and outputs the processed data to a first integrator. In this case, the first sensor 1312 includes an acceleration sensor, for example. Particularly, the first processor 1322 subtracts gravity from the data sensed by the first sensor 1312.

The second processor 1324 receives data sensed by a second sensor 1314, and processes the received sensing data. The processed data are output to the first processor 1322 and a mixer. In this case, the second sensor 1314 includes a gyro sensor, for example. Moving direction data may include yaw data, pitch data, roll data, etc. The second processor calculates a moving direction A of an insole of the smart shoes on the basis of the data sensed by the second sensor 1314.

The output data of the first integrator may be moving velocity data V, and the data processed by the second processor 1324 may be moving direction data A of the smart shoes wearer.

The data excluding the moving velocity data v1 from the output data of the first integrator, that is, moving distance data p0 are input to a second integrator and then accumulated. The moving velocity data v1, the output data of the second integrator, that is, moving distance data p1, and moving direction data a1 of the second processor 1324 are input to the filtering unit 1350. The filtering unit 1350 filters the moving velocity data v1, moving distance data p1 and moving direction data a1, which are input, using a Kalman filter which is mainly used in the aforementioned PDR algorithm. The input moving velocity data v1, moving distance data p1 and moving direction data a1 are filtered by the filtering unit 1350, whereby moving velocity data v2, moving distance data p2 and moving direction data a2 are output. The output moving velocity data v2, moving distance data p2 and moving direction data a2 are output to a mixer 1360.

The mixer 1360 includes a first mixer related to a moving distance, a second mixer related to a moving velocity, and a third mixer related to a moving direction.

The first mixer calculates final moving distance data P by mixing the moving distance data p1 which are the output of the second integrator with the moving distance data p2 which are the output of the filtering unit 1350.

The second mixer calculates final moving velocity data V by mixing the moving velocity data v1 extracted from the first integrator with the moving velocity data v2 which are the output of the filtering unit 1350.

The third mixer calculates final moving direction data A by mixing the moving direction data a1 which are the output of the second processor 1324 with the moving direction data a2 which are the output of the filtering unit 1350.

Figure 14:
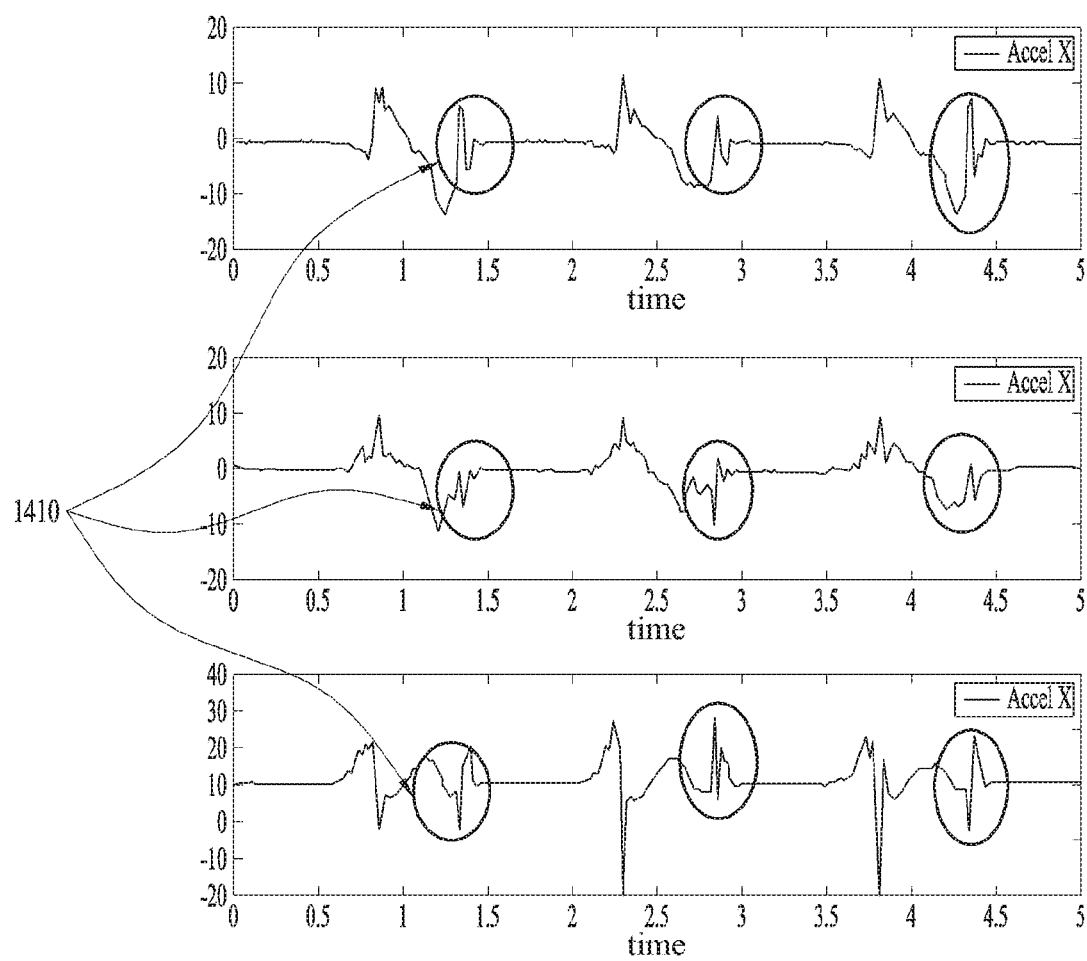
FIG. 14 is a smart shoes tracing data graph according to one embodiment of the present invention.

If the tracing data processor 1300 processes the tracing data of the smart shoes wearer by using the processor 1320 and the filtering unit 1350 of FIG. 13 on the basis of the sensing data of the sensor module mounted in the smart shoes, sensing data such as a graph shown in FIG. 14 may be obtained.

However, referring to FIG. 14, if the tracing data are processed based on only the data sensed by the first sensor 1312 and the second sensor 1314, every step of the smart shoes wearer may not be detected exactly due to a noise area 1410. This is because that one step of the smart shoes wearer may be missed as it is difficult to exactly measure zero velocity for every step of the smart shoes wearer in accordance with an effect of the noise and thus it is ambiguous to identify a previous step from next step. This may not cause a big problem in a state that the smart shoes wearer simply walks or does not move. However, if a moving velocity is increased or stride is narrow, it may affect an effect of whole data to cause an error. Therefore, since the error according to the noise area may affect reliability of the sensed tracing data, there may be a problem. Meanwhile, the noise area 1410 in this specification may not mean only an area where noise is generated but mean a point or area where an error may occur during data sensing related to the present invention.

To minimize or remove the error according to the noise, the present invention will be described with reference to sensing data of the aforementioned pressure sensor.

Referring to FIG. 13, the tracing data processor 1300 further includes a detector 1330 and a fourth mixer 1340.

The detector 1330 receives data sensed by a third sensor 1316, processes the received data, and outputs the processed data to the fourth mixer 1340. In this case, the third sensor 1316 may be the aforementioned pressure sensor according to the present invention. Therefore, the aforementioned description of the pressure sensor is applied to the third sensor, and the detailed description of the third sensor will be omitted. The data sensed by the pressure sensor may be generated per step of the smart shoes wearer. This may be a graph shown in FIG. 15 or 16.

The detector 1330 detects a zero velocity from the data input by being sensed by the third sensor 1316. The zero velocity may easily be detected from the graph data shown in FIG. 14, which are sensed as the third sensor 1316 is operated as a pressure switch according to every step of the wearer.

Zero velocity data z1 detected from the detector 1330 are mixed with the moving velocity data v1 extracted from the first integrator by the fourth mixer 1340, and the mixed data become an input v1' different from the input v1 of the filtering unit 1350. Afterwards, as described above, the data are filtered by the filtering unit 1350 and then moving distance P, moving velocity V and moving direction A data are calculated.

Figure 15:
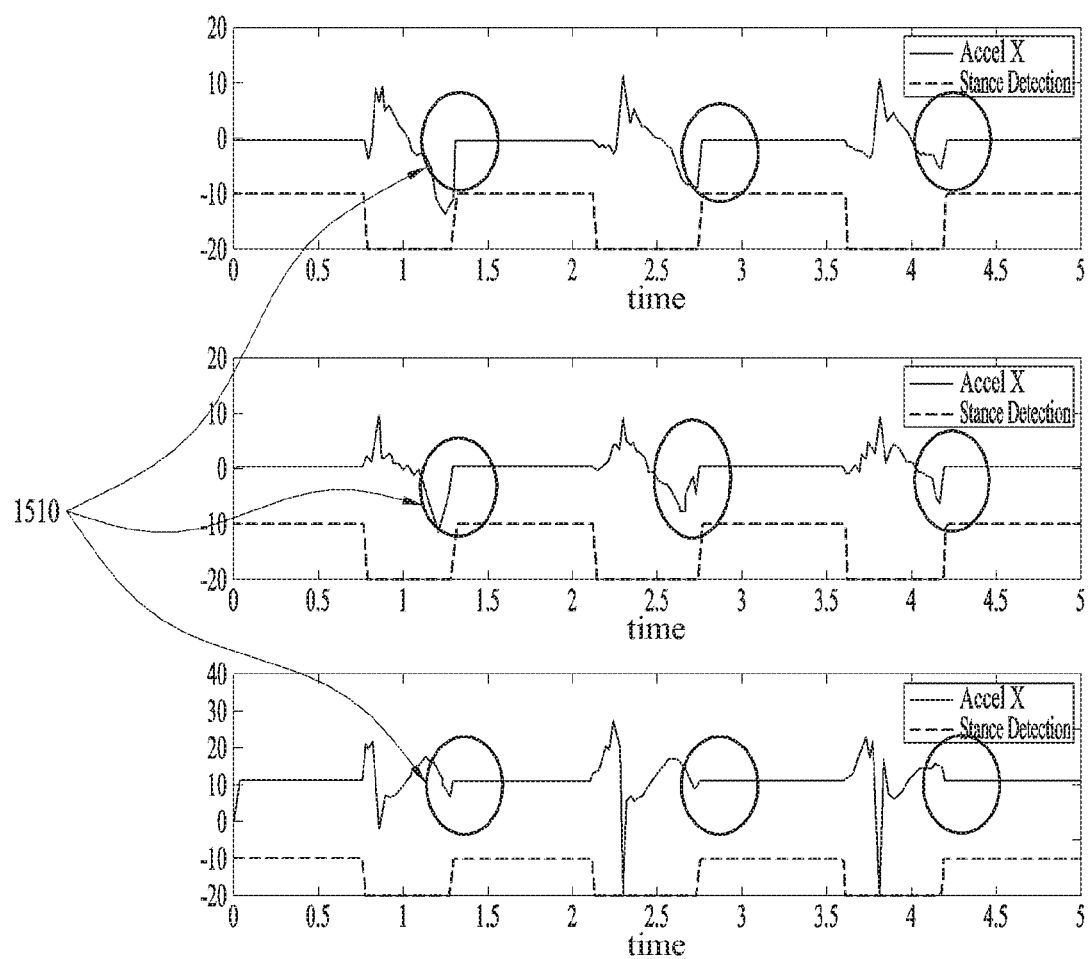
FIGS. 15 and 16 are smart shoes tracing data graphs according to another embodiment of the present invention.

This will be described with reference to FIGS. 14 and 15. As described above, the noise area 1410 exists in FIG. 14. However, referring to FIG. 15, the data 1510 filtered through the detector 1330 and the fourth mixer 1340 counterbalance the noise shown in FIG. 14 to minimize the zero velocity, whereby every step of the wearer may be recognized and processed definitely. Therefore, referring to FIG. 14, a portion that may be missed with respect to a specific step that may occur may be compensated, whereby exact data may be calculated.

Figure 16:
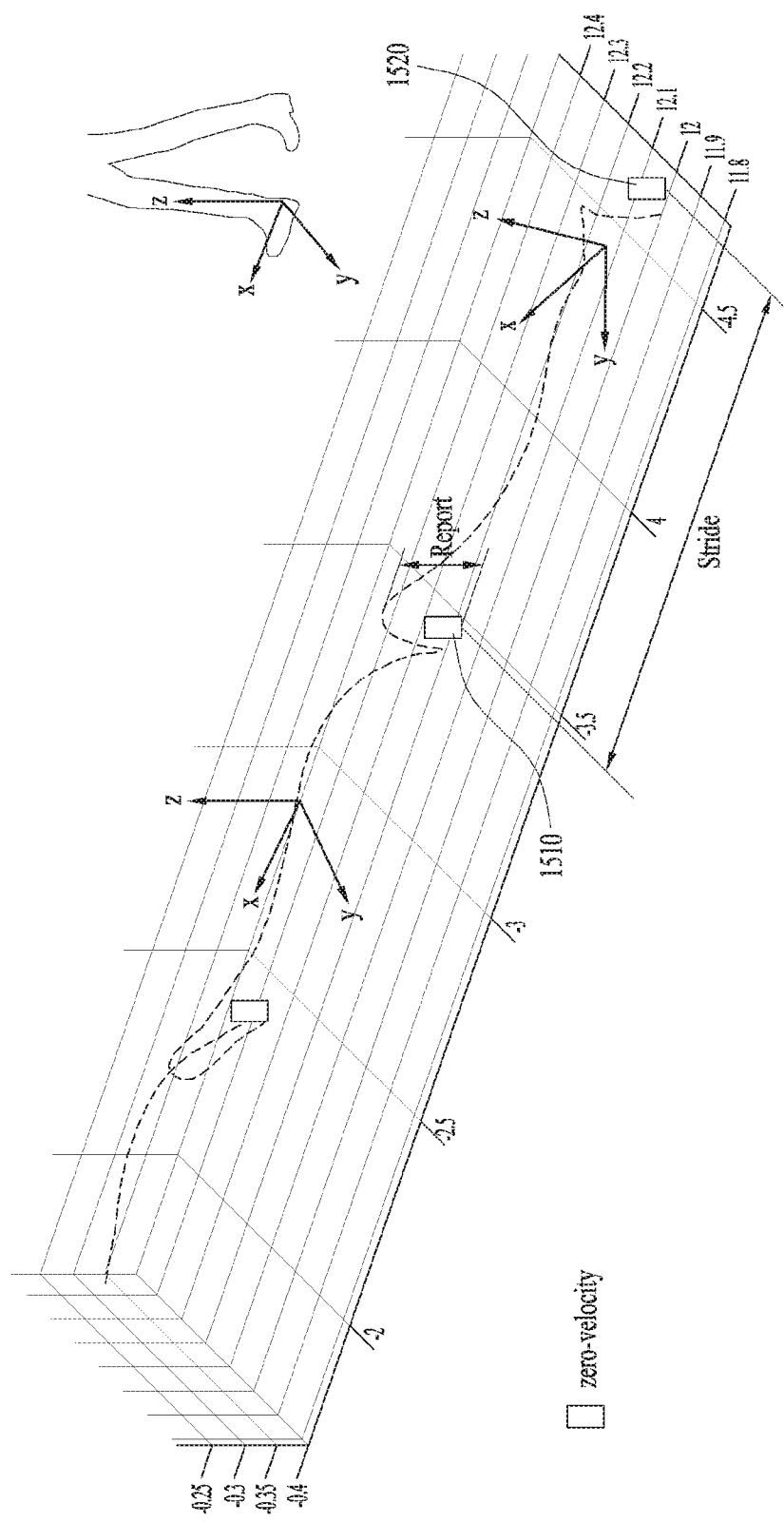

Therefore, referring to FIG. 16, the zero velocity is minimized with respect to movement data of the smart shoes wearer, that is, movement of axes x, y and z, whereby every step of the smart shoes wearer may be calculated exactly. Based on this result, according to the present invention including the PDR algorithm, foot angle data or foot angle correction data may be calculated easily and exactly, whereby step track, step velocity, step direction, stride and height of the smart shoes wearer may be calculated more easily and exactly as shown in FIG. 16. This may enhance efficiency of the system and reduce power consumption as compared with the case that correction is required due to the accumulated error as zero velocity of one step is not acquired exactly by the PDR sensor or inertia sensor only. Also, if only the data of the PDR sensor are used, wireless positioning calibration is required based on Wi-Fi or Bluetooth. However, if the data of the pressure data are also used, data sensing may be performed more exactly even without the wireless positioning calibration.

Also, in respect of stride or height, a barometer sensor based on altitude is used in case of hiking or building stairs in the related art. However, in this case, ambient pressure is rapidly changed due to weather change, wind, etc., or pressure change is serious and exact data sensing cannot be performed due to factors such as opening or closing of a window or door in case of stairs. Also, a problem occurs in that reliability of the sensed data is low. On the other hand, in the present invention, zero velocity is minimized based on the sensing data of the simple pressure sensor (pressure switch), whereby data may be calculated easily and exactly even without barometer sensor or other component.

The tracing data processing algorithm according to the present invention may be used for a movement information tracing and management service of the smart shoes wearer to measure calories consumption and weight change of the smart shoes wearer, and may automatically recognize bike riding, walking, running, etc. to enable navigation or scheduling service according to the recognized result. The tracing data processing algorithm of the present invention enables various services such as a step posture tracing and management service of a wearer (soldier, etc.), an indoor navigation service of mart, library, public institution, etc., a movement amount measurement and management service based on outdoor bike, walking navigation accuracy correction service, a tracing history management of a walking area, stride, and height, and a wearer tracing management service in a GPS or Wi-FI unavailable area.

Figure 17:
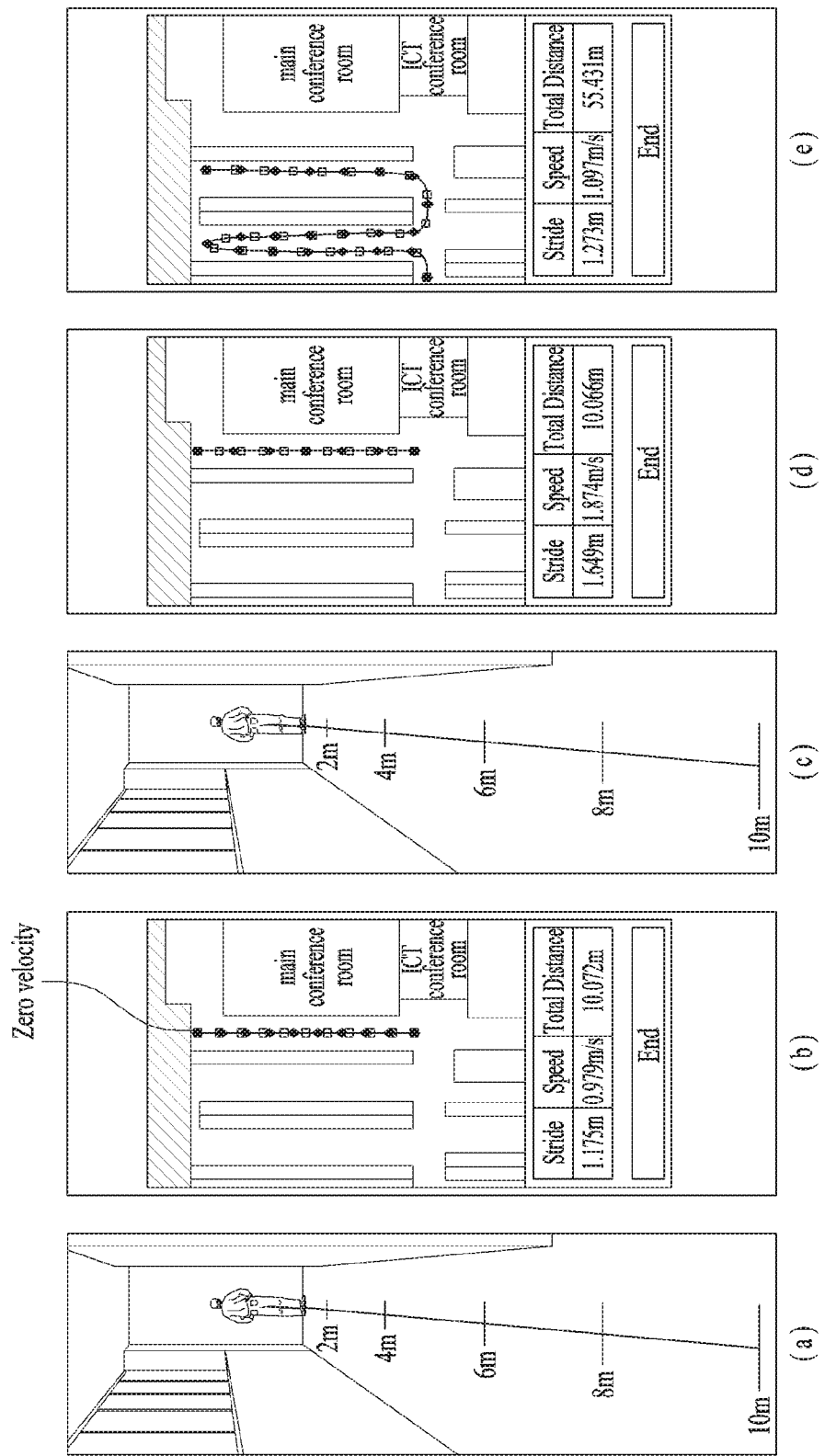
FIG. 17 is a view illustrating a UX of one example of a service scenario according to one embodiment of the present invention.

FIG. 17 is a view illustrating a UX of one example of a service scenario according to one embodiment of the present invention.

FIG. 17a illustrates a case that a wearer walks a moving distance of 10 m at an average velocity, and FIG. 17b is a UX of data acquired through the tracing data processor in FIG. 17a. In FIG. 17a, it is noted that the data acquired through the tracing data processor with respect to the moving distance of 10 m correspond to 10.072 m.

FIG. 17c illustrates a case that a wearer walks a moving distance of 10 m at a fast velocity, and FIG. 17d is a UX of data acquired through the tracing data processor in FIG. 17c. In FIG. 17c, it is noted that the data acquired through the tracing data processor with respect to the moving distance of 10 m correspond to 10.066 m.

In addition, FIG. 17e is a UX of stride, velocity and total distance data accumulatively acquired through the tracing data processor for a certain time.

Figure 18:
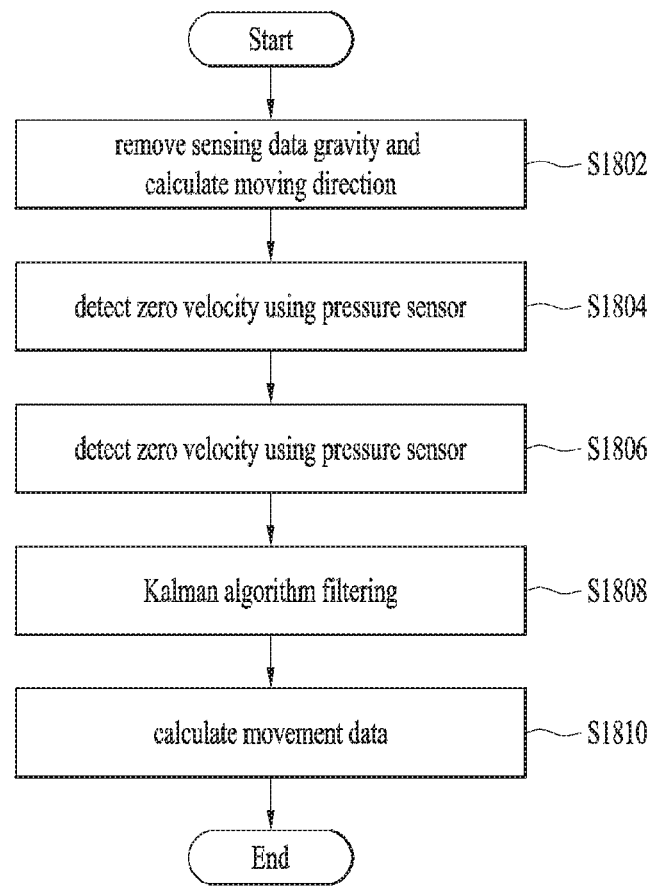
FIG. 18 is a flow chart illustrating a data processing method based on a tracing algorithm in a smart shoes system according to one embodiment of the present invention.

FIG. 18 is a flow chart illustrating a data processing method based on a tracing algorithm in a smart shoes system according to one embodiment of the present invention, According to the present invention, the tracing data processor of the smart shoes system receives sensing data from one or more first sensors (S1802), and detects zero velocity data by receiving the sensed data on the basis of an operation of a second sensor (S1804). In this case, the first sensors include the first sensor (acceleration sensor) and the second sensor (gyro sensor) of FIG. 13. Also, the second sensor includes the third sensor (pressure sensor) of FIG. 13.

The tracing data processor removes step noise of the sensing data received from the first sensors on the basis of the detected zero velocity data (S1806). The step noise means the noise 1410 shown in FIG. 14, and removal of the step noise means that the noise is processed as shown in FIG. 15.

The tracing data processor filters the sensing data from which the step noise is removed (S1808).

The tracing data processor acquires movement data of the smart shoes on the basis of the filtered sensing data and a predetermined threshold value (S1810). The predetermined threshold value may indicate a value according to data standardization based on filtering of the filtering unit. In this way, data standardization may be helpful for data management.

Figure 19:
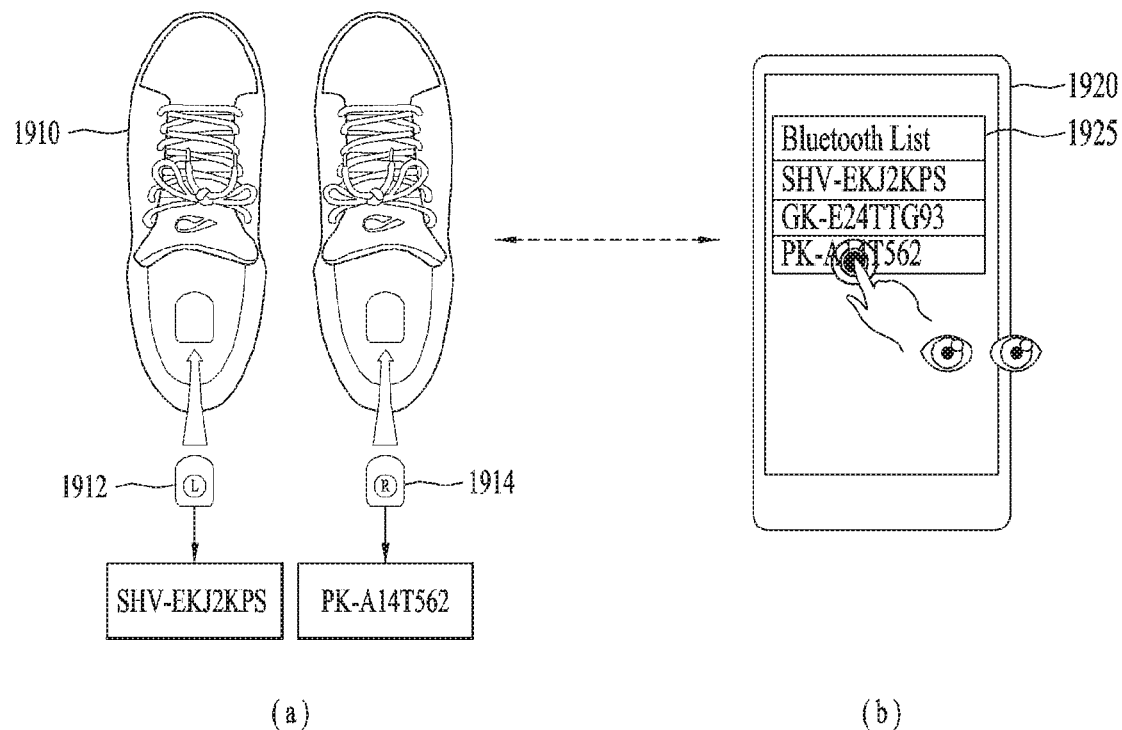
FIGS. 19 and 20 are views illustrating a pairing procedure between smart shoes and a mobile terminal in accordance with the present invention.
Figure 20:
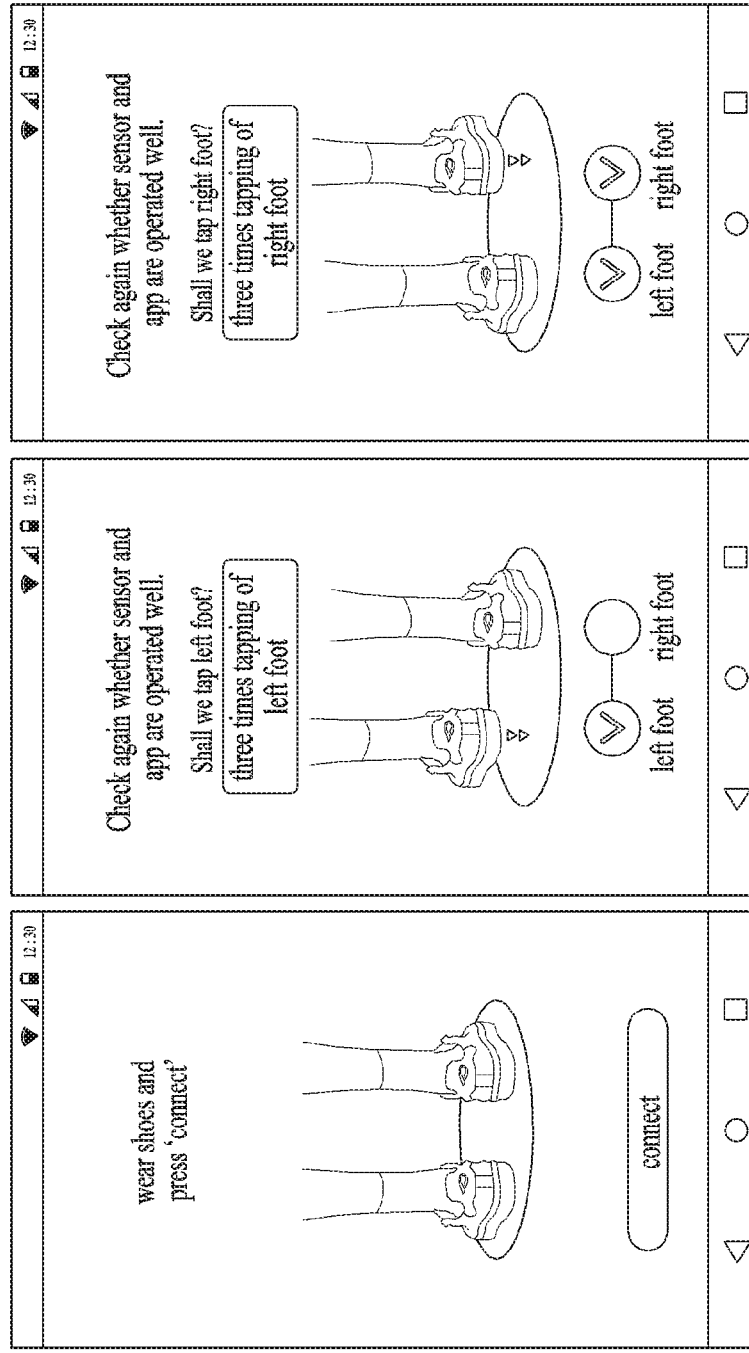

FIGS. 19 and 20 are views illustrating a pairing procedure between smart shoes and a mobile terminal in accordance with the present invention.

Based on the aforementioned embodiments, movement data may be sensed from smart shoes 1910, and a mobile terminal 1920 may acquire meaningful data from the data sensed from the smart shoes 1910. At this time, to actively perform data communication between the smart shoes 1910 and the mobile terminal 1920, a pairing procedure for data communication between them should be preceded.

For convenience, in this specification, it is assumed that the data communication is performed based on a Bluetooth communication protocol. Therefore, pairing for the data communication is performed in accordance with definition in the Bluetooth communication protocol. However, in this case, the communication protocol is not limited to the Bluetooth communication protocol, and may include all communication protocols currently defined for data communication, such as Wi-Fi, LTE, and ZigBee, or communication protocols which will be defined later.

Meanwhile, only one communication protocol is not used for the data communication. A plurality of communication protocols may be used in accordance with various criteria such as data amount and data attributes. For example, a predetermined communication protocol may exist for urgent data processing such as emergency alert message (EAS). In addition, another communication protocol may be used if data communication is not performed actively in accordance with a communication condition.

Referring to FIG. 19a, a first smart shoes sensor module 1912 is mounted in a left (L) smart shoe constituting the smart shoes, and a second smart shoes sensor module 1914 is mounted in a right (R) smart shoe. The first smart shoes sensor module 1912 and the second smart shoes sensor module 1914 may have their unique identification data in accordance with a communication protocol for data communication. For example, referring to FIG. 19a, the first smart shoes sensor module 1912 has unique identification data called 'SHV-EK.J2KPS' for data communication, and the second smart shoes sensor module 1914 has unique identification data called 'PK-A14TS62' for data communication.

The unique identification data may be given during a manufacturing step of the smart shoes in accordance with a manner scheduled or defined by a corresponding communication protocol in case of a predetermined communication protocol, for example, Bluetooth. Even though the unique identification data are given for a specific communication protocol, the unique identification data may be used when another communication protocol is used. The unique identification data may be given for common use from the time when the smart shoes are manufactured. Alternatively, the unique identification data may be changed randomly by a user for identification convenience of the user within the range that does not affect data communication or a manner defined in the communication protocol.

The mobile terminal 1920 may provide an available Bluetooth communication list 1925 on its screen as shown in FIG. 19b if the mobile terminal enables or turns on Bluetooth communication for data communication.

Therefore, the user may perform pairing by selecting a desired device from the list provided on the mobile terminal 1920. However, at this time, if a password is set to the selected device, the pairing procedure may be completed through password input together with appropriate UX. Also, when pairing is completed, it is difficult for the user to identify whether pairing has been performed normally. Therefore, smart shoes shaped UX may be provided on the screen of the mobile terminal in accordance with the system to allow the user to view the pairing procedure, or a feedback such as vibration may be given from the paired smart shoes to the user, whereby the user may easily recognize the result of the pairing.

Unlike FIG. 19, in FIG. 20, automatic pairing may be performed based on the result according to a predetermined activity of the smart shoes wearer without the separate list shown in FIG. 19b. This may be helpful for more intuitive and convenient pairing under various statuses that the user cannot touch or input the mobile terminal or it is difficult for the user to select a desired device due to too many device lists which are provided.

As shown in FIG. 20a, if the user wears the smart shoes and pushes or selects connection in accordance with a guide on the UX, the mobile terminal 1920 requires additional operation for pairing as shown in FIGS. 20b and 20c. If a pairing request with the smart shoes is selected by the mobile terminal in FIG. 20a, the smart shoes wearer is requested to tap a left foot three times to identify whether a sensor and an application are operated well in FIG. 20b. If the smart shoes wearer performs the operation according to the request of the mobile terminal, the left (L) smart shoes sensor module and the mobile terminal are automatically registered and paired. Afterwards, if the smart shoes wearer performs the operation requested for the right (R) smart shoes sensor module in FIG. 20c like FIG. 20b, the mobile terminal automatically performs registration and pairing. FIGS. 20b and 20c are intended for registration and pairing of both the left and right smart shoes sensor modules, and the order of registration and pairing thereof is random and is not important. If the sensor module is mounted in any one of the smart shoes, any one of FIGS. 20b and 20c is performed.

In FIG. 20, the mobile terminal performs a previous identification function as to whether active data communication is performed as well as automatic registration and pairing of the sensor modules mounted in the smart shoes. Also, since it is difficult for the user to determine whether data sensing is performed normally if the operations shown in FIG. 20 are not performed, a calibration task for more exact data sensing may be performed. For example, through FIG. 20b or 20c, the user may intuitively recognize intensity or level of a pressure for recognizing a step of the smart shoes wearer, and an error operation of the sensor module may be determined. As a result, the user may calibrate sensing sensitivity of the sensor module as the case may be. In other words, the sensor module of the smart shoes may have predetermined sensing sensitivity and a threshold pressure reference on the basis of average data.

However, since the level of data sensing felt by the corresponding user may be varied even based on the reference, this may be easily calibrated through the procedure of FIG. 20b or 20c. For example, as described above, it is assumed that the user has performed the procedure shown in FIG. 20b or 20c for pairing. In this procedure, if the smart shoes wearer feels that data sensing is performed differently, the smart shoes wearer requests threshold pressure calibration, and the threshold pressure calibration is provided in the form similar to the UX provided in FIG. 20b or 20c, whereby the threshold pressure is controlled as desired by the user. In this case, the threshold pressure controlled or calibrated in FIG. 20b or 20c is transmitted from the mobile terminal to the smart shoes, and the controller of the smart shoes may control the sensor module based on the threshold pressure or re-classify or modify the data sensed by the sensor module.

Meanwhile, pairing has been performed through the operation such as tapping feet of the smart shoes wearer in FIG. 20, but the present invention is not limited to the number of times of tapping feet or tapping feet. Pairing may be performed through various operations that may be performed easily by the smart shoes wearer. Meanwhile, various operations in addition to the tapping feet, that is, a list for pairing may be provided and a pairing procedure may be performed in accordance with the operation selected by the user. In this case, the operation selected by the user may be used during execution of an application or for identification of the corresponding user. Alternatively, after paring request with the smart shoes, the mobile terminal may automatically pair with the smart shoes if a signal is continuously received in the smart shoes not a given pattern. Meanwhile, the mobile terminal may automatically pair with a device having the greatest signal intensity, that is, the smart shoes during pairing request.

Meanwhile, in respect of the present invention, the mobile terminal may identify the left (L) smart shoe from the right (R) smart shoe through a given gesture input if the sensor of the smart shoes, especially the gyro sensor has three axes. The mobile terminal may automatically identify the left (L) smart shoe from the right (R) smart shoe by comparing data received from each sensor module with each other without separate identification of the left (L) smart shoe from the right (R) smart shoe in case of 9-axis sensor (acceleration sensor of 3 axes, gyro sensor of 3 axes, and terrestrial magnetic sensor of 3 axes).

Moreover, if the mobile terminal registers a smart shoes application as a basic application, the mobile terminal may perform various operations such as lock and release of the mobile terminal, execution of a specific function, execution of a specific application, and control of the executed application on the basis of a predetermined operation of the smart shoes wearer.

In addition, request, selection and function execution related to the smart shoes on the mobile terminal may be performed in various manner such as voice, gesture and eye-tracking as well as a touch of the mobile terminal, or may be performed by combination of the above manners.

However, the procedure of FIG. 20 may be performed together with the procedure of FIG. 19. For example, after pairing in FIG. 19, start or end of actual data communication may be performed through the procedure of FIG. 20, or vice versa.

Meanwhile, referring to FIGS. 19 and 20, if the mobile terminal 1920 performs initial pairing with the smart shoes 1910 or performs pairing through the smart shoes application, the mobile terminal may perform automatic pairing on the basis of pairing data which are previously stored. However, at this time, if the smart shoes application is used by the mobile terminal 1920, a list based on unique identification data of the smart shoes sensor modules shown in FIG. 19b is provided during initial pairing. However, unlike the aforementioned description, Bluetooth unique identification data of the mobile terminal not the smart shoes may be provided by filtering from the above list. Also, the aforementioned automatic pairing may acquire sensing data and calculate various movement data based on the tracing algorithm through setup or considering a previous use pattern of the user even without additional operation or input of the user and therefore automatically acquire and calculate the smart shoes data according to the acquired result and the calculated result and provide related UX.

Figure 21:
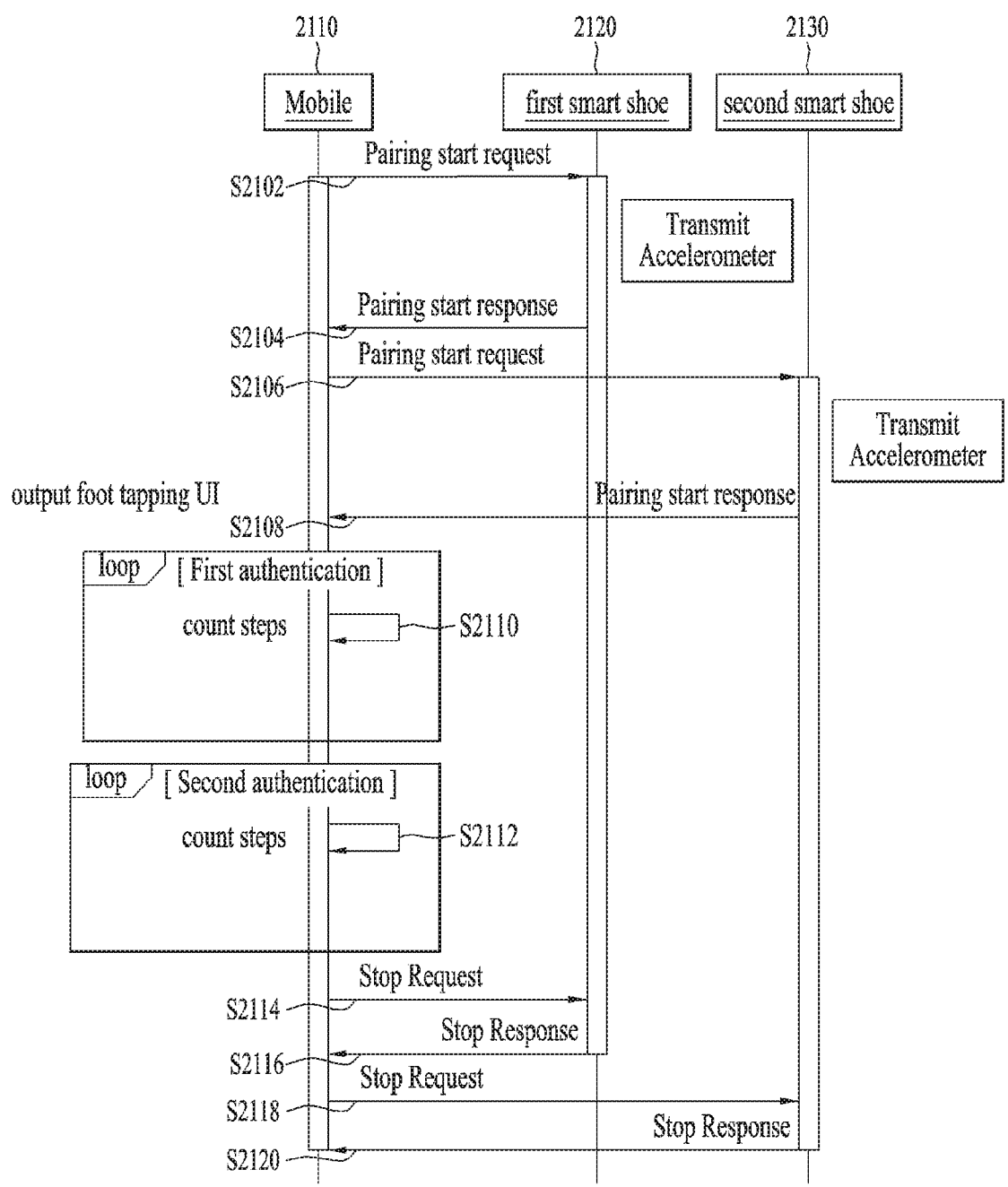
FIGS. 21 and 22 are sequence diagrams illustrating a procedure of automatically pairing smart shoes and a plurality of mobile terminals in accordance with one embodiment of the present invention.
Figure 22:
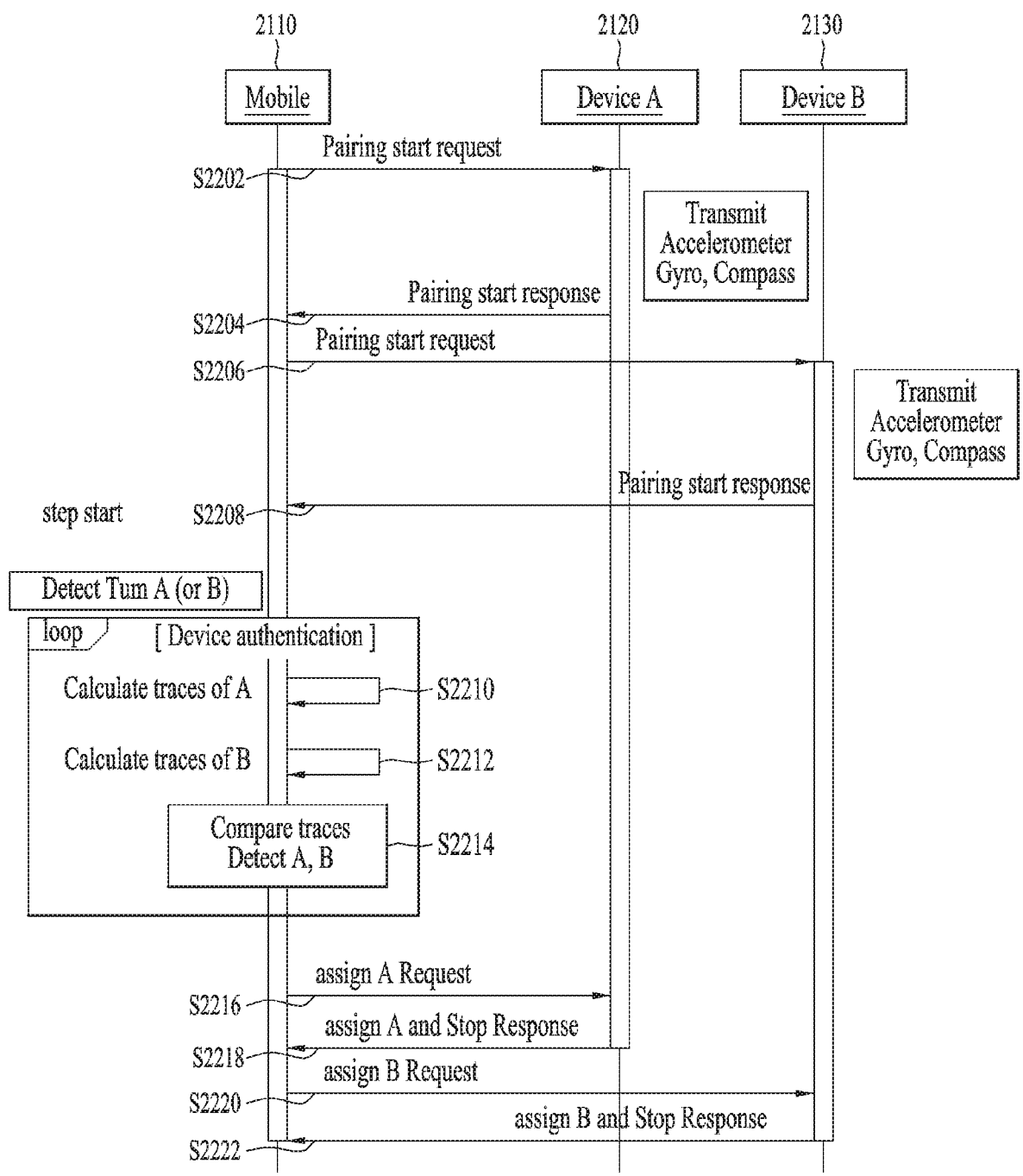

FIGS. 21 and 22 are sequence diagrams illustrating a procedure of automatically pairing smart shoes and a plurality of mobile terminals in accordance with one embodiment of the present invention.

For example, FIG. 21 illustrates a pairing procedure through a gesture between the mobile terminal and the smart shoes provided with a 3-axis sensor, and FIG. 22 illustrates a pairing procedure through a gesture between the mobile terminal and the smart shoes provided with a 9-axis sensor.

First of all, the pairing procedure through a gesture between the mobile terminal 2110 and the first and second smart shoes 2120 and 2130 will be described in more detail with reference to FIG. 21. At this time, the first smart shoe 2120 indicates a left (L) smart shoe that includes a 3-axis based smart shoes sensor module, and the second smart shoe 2130 indicates a right (R) smart shoe that includes a 3-axis based smart shoes sensor module.

The mobile terminal 2110 transmits a pairing start request signal to the first smart shoe 2120 (S2102). At this time, the first smart shoe 2120 enables the pairing start request signal of the mobile terminal 2110 by transmitting the pairing start request signal to the sensor module. The first smart shoe 2120 returns a pairing start response signal in response to the pairing start request signal of the mobile terminal 2110 (S2104). Generally, the returning pairing start response signal of the first smart shoe 2120 includes a response that agrees to the pairing start request.

Then, the mobile terminal 2120 transmits a pairing start request signal to the second smart shoe 2130 (S2106). At this time, the second smart shoe 2130 enables the pairing start request signal of the mobile terminal 2110 by transmitting the pairing start request signal to the sensor module. The second smart shoe 2130 returns a pairing start response signal in response to the pairing start request signal of the mobile terminal 2110 (S2108).

The steps S2102 to S2104 or the steps S2106 to S2108 are performed if the smart shoes sensor module is mounted in the corresponding shoe. Therefore, if the sensor module is mounted in both the smart shoes, all the steps S2102 to S2108 are performed. However, if the sensor module is mounted in any one smart shoe, either the steps S2102 to S2104 or the steps S2106 to S2108 may be performed. Also, the order of the steps S2102 to S2104 or the steps S2106 to S2108 may be different from the shown order.

The aforementioned steps S2102 to S2108 are connection steps for pairing, and may be regarded as pairing initial steps.

In this way, after the pairing initial steps are performed, the mobile terminal 2110 provides the UX shown in FIG. 19 or 20 to attempt pairing with the smart shoes.

In more detail, the mobile terminal 2110 performs an authentication procedure with the first smart shoe 2120. Referring to FIG. 20, this authentication procedure is performed through tapping foot of the smart shoes wearer with respect to the first smart shoe as much as the number of given times. At this time, the mobile terminal 2110 counts the number of times for tapping foot of the first smart shoe 2120 (S2110), and authenticates the corresponding smart shoe if tapping foot reaches the given count times. At this time, this step may be performed repeatedly in the form of loop until authentication is successfully performed.

Meanwhile, if authentication is failed a predetermined number of times or more or is not successfully performed within a predetermined time, the authentication procedure may be reset and then return to the pairing initial step or execution of the application for pairing on the mobile terminal 2110 may end.

The authentication procedure of the mobile terminal 2100 with respect to the first smart shoe 2120 is performed equally with respect to the second smart 2130.

If the pairing authentication procedure for both the smart shoes is completed through the steps S2110 and S2112, the mobile terminal 2110 transmits a pairing step request signal to each of the smart shoes 2120 and 2130 (S2114, S2118), and receives a response signal to the pairing step request signal from each of the smart shoes 2120 and 2130 (S2116, S2120).

Through the aforementioned procedure, the pairing procedure is completed, and data communication between the mobile terminal 2110 and the smart shoes 2120 and 2130 is performed.

Meanwhile, the procedure shown in FIG. 21 is not limited to the shown order. For example, the steps S2106 to S2108 may be performed after the step S2110 or the step S2114.

Next, the pairing procedure through a gesture between the mobile terminal 2110 and the first and second smart shoes 2120 and 2130 will be described in more detail with reference to FIG. 22. At this time, the first smart shoe 2120 indicates a left (L) smart shoe that includes a 9-axis based smart shoes sensor module, and the second smart shoe 2130 indicates a right (R) smart shoe that includes a 9-axis based smart shoes sensor module.

Since the procedure of FIG. 22 is the same as the pairing initial step between the mobile terminal 2110 and the smart shoes 2120 and 2130 in FIG. 21, its repeated description will be omitted. However, sensors enabled based on the 9-axis sensor at the pairing initial step of FIG. 22 may be more than those enabled based on the 3-axis sensor at the pairing initial step of FIG. 21.

Meanwhile, after the pairing initial step in FIG. 22, the pairing authentication step is different from that of FIG. 21. For example, the mobile terminal 2110 provides an authentication UX and thus receives a gesture input of the smart shoe in FIG. 21, whereas an authentication procedure different from that of FIG. 21 is used in FIG. 22. In other words, the mobile terminal 2110 detects at least one of the first smart shoe 2120 and the second smart shoe 2130 (S2210).

The mobile terminal 2110 authenticates the detected smart shoe. At this time, it is assumed that the first smart shoe 2120 and the second smart shoe 2130 have been detected. The mobile terminal 2110 calculates traces of the first smart shoe 2120 (S2212), and equally calculates traces of the second smart shoe 2130 (S2214). The mobile terminal 2110 compares the calculated traces of the first smart shoe 2120 with the calculated traces of the second smart shoe 2130 (S2216). In this case, the mobile terminal 2110 may compare a trace calculate value of each smart shoe, which is previously stored in the mobile terminal 2110 (or server, etc.) with the trace calculated value of each smart shoe, which is calculated through the steps S2212 and S2214, to perform authentication. However, the present invention is not limited to this case, and may use various targets, which may recognize or authenticate each smart shoe, in respect of the comparison.

As a result of the step S2216, if authentication of at least one of the smart shoes is failed, the mobile terminal 2110 may again perform the aforementioned authentication procedure for the corresponding shoe or both the smart shoes. In other words, the authentication procedure may be performed repeatedly in the form of a loop structure. Meanwhile, this repetition may be performed for a predetermined number of times, or may be re-performed by resetting the pairing procedure for the smart shoe of which authentication is finally failed or both the smart shoes.

As a result of the step S2216, if each smart shoe is authenticated, the mobile terminal 2110 advances to next procedure. Referring to FIG. 22, the mobile terminal 2110 transmits a 'LEFT' request allocation signal to the first smart shoe 2120 (S2218), and the first smart shoe 2120 returns a 'LEFT and Stop' response allocation signal (S2220). A request-response procedure of the first smart shoe is performed equally even with respect to the second smart shoe (S2222, S2224).

Through the aforementioned procedure, the pairing procedure between the mobile terminal 2110 and the smart shoes 2120 and 2130 provided with a 9-axis sensor may be completed, and after the pairing procedure is completed, data communication may be performed.

The pairing procedure between the smart shoes provided with the 3-axis sensor and the mobile terminal and the pairing procedure between the smart shoes provided with the 9-axis sensor and the mobile terminal in FIGS. 21 and 22 are only exemplary, and are not limited to the shown sequences. Also, each sequence of the paring procedures shown in FIGS. 21 and 22 may not be an essential sequence. At least one sequence may be omitted or skipped, whereas at least one sequence may be added depending on system or status.

The steps of the first smart shoe 2120 and the second smart shoe 2130 in the steps shown in FIG. 21 may be performed in reverse order. For example, in FIG. 21 the first smart shoe 2120 accesses the mobile terminal prior to the second smart shoe 2130, or vice versa. This may equally be applied to FIG. 22.

Meanwhile, in this specification, it is assumed that the sensor module is mounted in each of both the smart shoes. However, as shown in FIGS. 21 and 22, it is not required that pairing initialization and pairing authentication should be performed for both the smart shoes. For example, if the pairing procedure is completed with respect to any one smart shoe, the other smart shoe may be paired automatically as a set or pair without authentication. If an error or problem occurs during later data communication, authentication may newly be performed or re-authentication may be performed.

Hereinafter, a method for exactly calculating movement data for activity of a user who wears smart shoes, for example, exactly calculating activity amount of the user by identifying stairs movement of the user from flatland movement will be described in detail. In this way, movement data of the user who wears smart shoes may be detected exactly to calculate activity amount, and motion guide data may be provided based on the detected movement data and the calculated activity amount, whereby satisfaction of the user may be improved and reliability of the smart shoes may be improved.

Recently, various devices such as smart watch or smart shoes, which measure activity amount of a user, have been introduced in the market. The devices measure a total activity amount of a user in a daily unit and notify the user of the total activity amount. However, although the user performs various movements which become a basis of measurement for activity amount, the devices of the related art may fail to measure the corresponding movements or regard the movements as one movement. For example, the user may walk on a flatland or go up and down stairs as various movements. It is general that the devices of the related art may fail to identify walking on the flatland from going up and down stairs, or may recognize these movements as the same movement. Unlike the flatland movement, the movement of stairs i) increases lung capacity by increasing short-time oxygen consumption to the utmost limit, ii) trains a muscle for unfolding backbone by straightening one's back through going up stairs, iii) is effective for strengthening a muscle (for example, musculus quadriceps femoris) corresponding to the front part of thigh that occupies 30% of a body muscle, iv) prevents falling and fracture by increasing body balance through alternative movement of both legs, v) decreases a risk of death caused by myocardial infarction with respect to a person who goes up stairs 20 floors or more every week, vi) improves a cardio pulmonary function by reducing a heart rate like jogging through continuous stairs movement, vii) increases muscle amount, basic metabolism and reduces body fat and fat on stomach, and viii) reduces knee cartilage strain and prevents degenerative arthritis by training muscles surrounding knee. Therefore, in addition to the aforementioned medical effects, as the movement of stairs is available everywhere in daily life, may train lower body muscles for a short time, and needs calorie consumption more than flatland walking, the movement of stairs is favorable for diet and may predict a risk of occurrence of cardiovascular disorders through a breathless level. In this respect, it is required to exactly recognize the movement of stairs. However, since the devise of the related art fail to exactly recognize the movement of stairs, an error exists in calculation of activity amount. This causes a gap between activity actually felt by a user and activity measured through the devices of the related art to affect reliability of the devices.

The user who wears the smart shoes may perform various movements even within a predetermined time unit. Conventionally, the smart shoes of the related art relate to flatland, and recognize a slope or stairs as flatland even though the user goes up and down the slope or stairs and calculate activity amount based on the recognized result. Therefore, the smart shoes of the related art may provide data different from activity level or activity amount felt by the user. This is a factor that reduces reliability of the user with respect to the smart shoes.

Therefore, the present invention is intended to provide the user with exact data by exactly recognizing stairs movement of the user who wears the smart shoes and calculating the activity amount based on the recognized result. Meanwhile, this stairs movement may be combined with data on flatland in addition to stairs, whereby exact data with respect to movement of the user in a predetermined time unit may be provided unlike the related art. Meanwhile, according to the present invention, calibration data of the stairs movement may be provided from stairs movement data of the user who wears the smart shoes, and analysis resultant data and calibration data of the stairs movement data may be fed back to the user.

Hereinafter, stairs movement sensing in addition to flatland movement sensing of the user who wears the smart shoes will be described with reference to the accompanying drawings. The description related to configuration of the smart shoes and data communication will be understood with reference to the disclosure or related description(s) in at least one of FIGS. 1 to 22.

FIG. 23 is a view illustrating sensors or sensor combination for stairs movement sensing related to the present invention.

The smart shoes according to the present invention are provided with a pressure sensor. However, if the pressure sensor is provided at a specific position only of the smart shoes, it may be difficult to exactly recognize stairs movement unlike flatland.

Generally, the user allows a part of an insole and midsole of the smart shoes not the entire of the insole and midsole to be in contact with stairs based on height and width of the stairs. For example, if the smart shoes are divided into a front part where toes are arranged and a rear part of heel based on a center of a sole, it is general that most of users step a floor of stairs by using the front part only. Therefore, in this case, if the pressure sensor according to the present invention is provided on the rear part only, it is difficult to perform pressure sensing according to a contact with the floor of the stairs in view of a property of the pressure sensor, whereby it may be difficult to exactly recognize the stairs movement. If the pressure sensor according to the present invention is provided on the front part, the stairs movement may be recognized exactly.

Hereinafter, recognition of movement of the user who wears the smart shoes through at least one another sensor instead of the pressure sensor or together with the pressure sensor will be described. In this case, examples of another sensor may include a barometer sensor, an acceleration sensor, a gyro sensor, and a magnetic sensor as shown in FIG. 23*a*.

Referring to FIG. 23*a*, the user who holds a smart terminal provided with a barometer sensor with a hand wears smart shoes provided with at least one of a pressure sensor, an acceleration sensor, a gyro sensor, a magnetic sensor, and a barometer sensor and moves on the stairs.

The aforementioned sensors may be combined in various types and used as recognition sensors of stairs movement related to the present invention. However, as shown in FIG. 23*b*, a method for recognizing stairs movement of the user who wears the smart shoes through combination of the acceleration sensor, the gyro sensor and the magnetic sensor has problems in that the amount of computation is complicated and power consumption is high. Therefore, considering a low power to be suitable for the need of the smart shoes, stairs movement sensing of the user who wears the smart shoes through the acceleration sensor will be described in accordance with the present invention. At this time, in addition to the acceleration sensor, the pressure sensor according to the present invention may be used.

Figure 24:
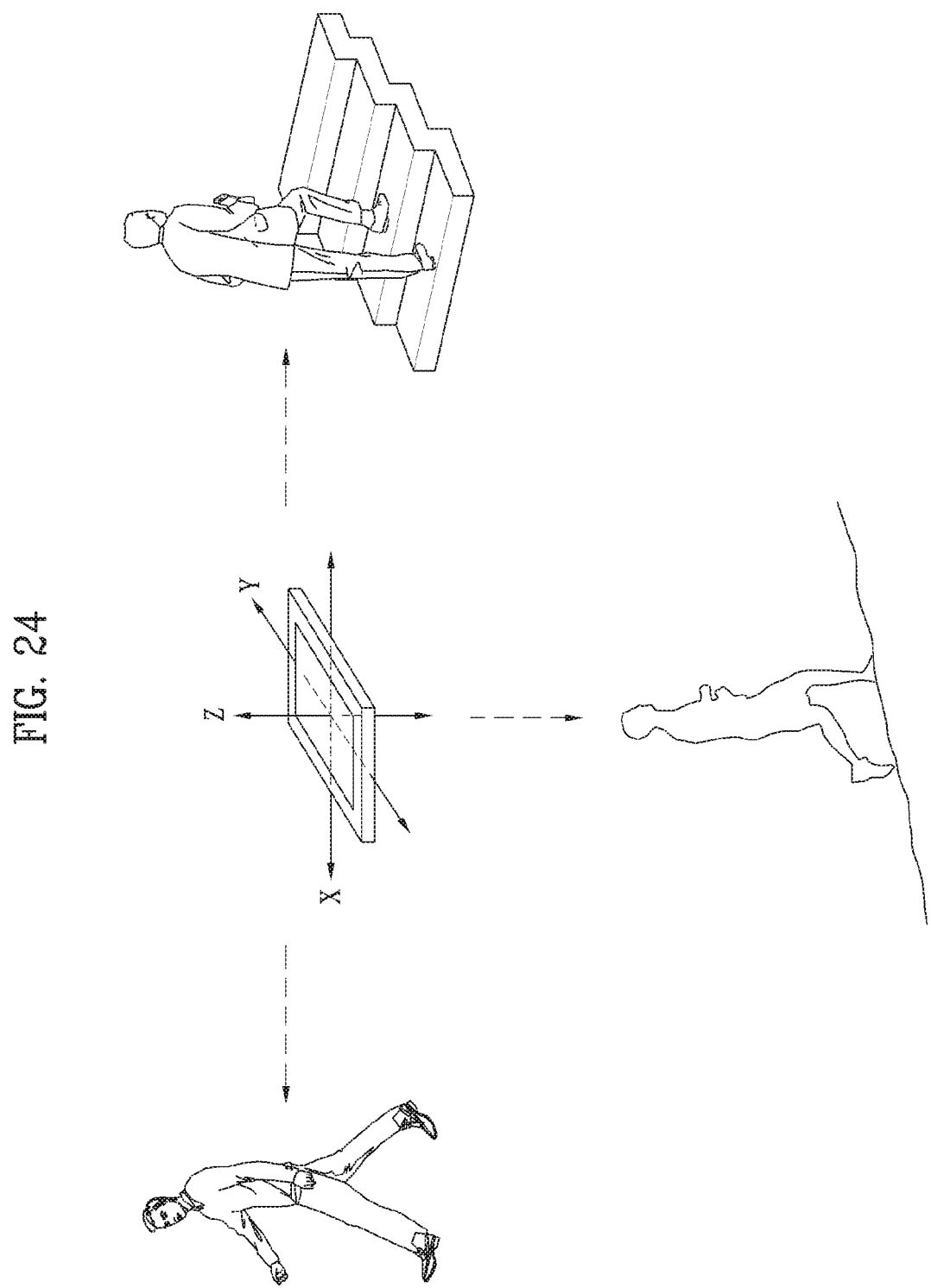
FIG. 24 is a view illustrating movements identified in description of stairs movement sensing according to the present invention.

FIG. 24 is a view illustrating movements identified in description of stairs movement sensing according to the present invention.

In FIG. 24, identification of flatland movement and ascending/descending movement of a slope way with respect to stairs movement sensing according to the present invention will be described.

For example, a method for identifying flatland movement, slope way movement and stairs movement on the basis of an acceleration sensor 2410 provided in the smart shoes will be described in FIG. 24.

First of all, stairs movement and flatland movement of the user who wears the smart shoes may be identified from each other through axes x and z of the acceleration sensor. In other words, the stairs movement and the flatland movement are identified from each other through a stride (X-axis) of the user who wears the smart shoes and a vertical ascending level (Z-axis) of the smart shoes at every step. For example, it is general that the stairs movement of the user who wears the smart shoes has a stride (X-axis) smaller than or equal to that of the flatland movement and a vertical ascending level (Z-axis) greater than that of the flatland movement. Therefore, the flatland movement and the stairs movement may be identified from each other through sensing values of axes x and z of the acceleration sensor of the smart shoes. At this time, if there are reference data for the flatland movement and the stairs movement, the flatland movement and the stairs movement may be identified from each other more easily.

Also, the stairs movement and slop way movement of the user who wears the smart shoes may be identified from each other through at least two or more axes x, y and z of the acceleration sensor. In other words, the stairs movement and the slope way movement may be identified from each other through a sensor position at a stride (X-axis) time of the user who wears the smart shoes.

In respect of identification of the stairs movement and the slope way movement, considering a slope angle of the slope way, each movement may have an identified pattern value of at least one of axes x, y and z of the acceleration sensor provided in the smart shoes. For example, if the slope angle of the slope way is between the flatland and the stairs, sensing values of the acceleration sensor, which are sensed by stairs movement, may have a different pattern value in at least one of axes x, y and z from sensing values of the acceleration sensor, which are sensed by slope way movement. In this case, the difference pattern value occurs in the axis z, and the value of the axis y in the slope way may not have a fixed or constant pattern as compared with stairs movement. As a result, the slope way movement and the stairs movement may be identified from each other. Meanwhile, even in the case that the slope angle of the stairs and the slope angle of the slope way are similar to or equal to each other, values sensed through the acceleration sensor, especially sensing values of at least one or more of the axes x, y and z may have different patterns in each case as described above.

The stairs movement and the flatland or slope way movement may be identified from each other additionally using the pressure sensor provided in the smart shoes. It is assumed that the pressure sensor is located at the rear part of the smart shoes. In this case, if the sensing value of the acceleration sensor and the sensing value of the pressure sensor are predetermined values or less, the stairs movement may be identified from the flatland movement or slope way movement.

The identification of each of the aforementioned movements will be described in more detail through a sensing graph which will be described later. However, for convenience, stairs movement and flatland movement will be described as an example. Also, the movements will be described with reference to sensing data of the acceleration sensor and the gyro sensor of the smart shoes. However, the present invention is not limited to the sensing data of the acceleration sensor and the gyro sensor.

Figure 25:
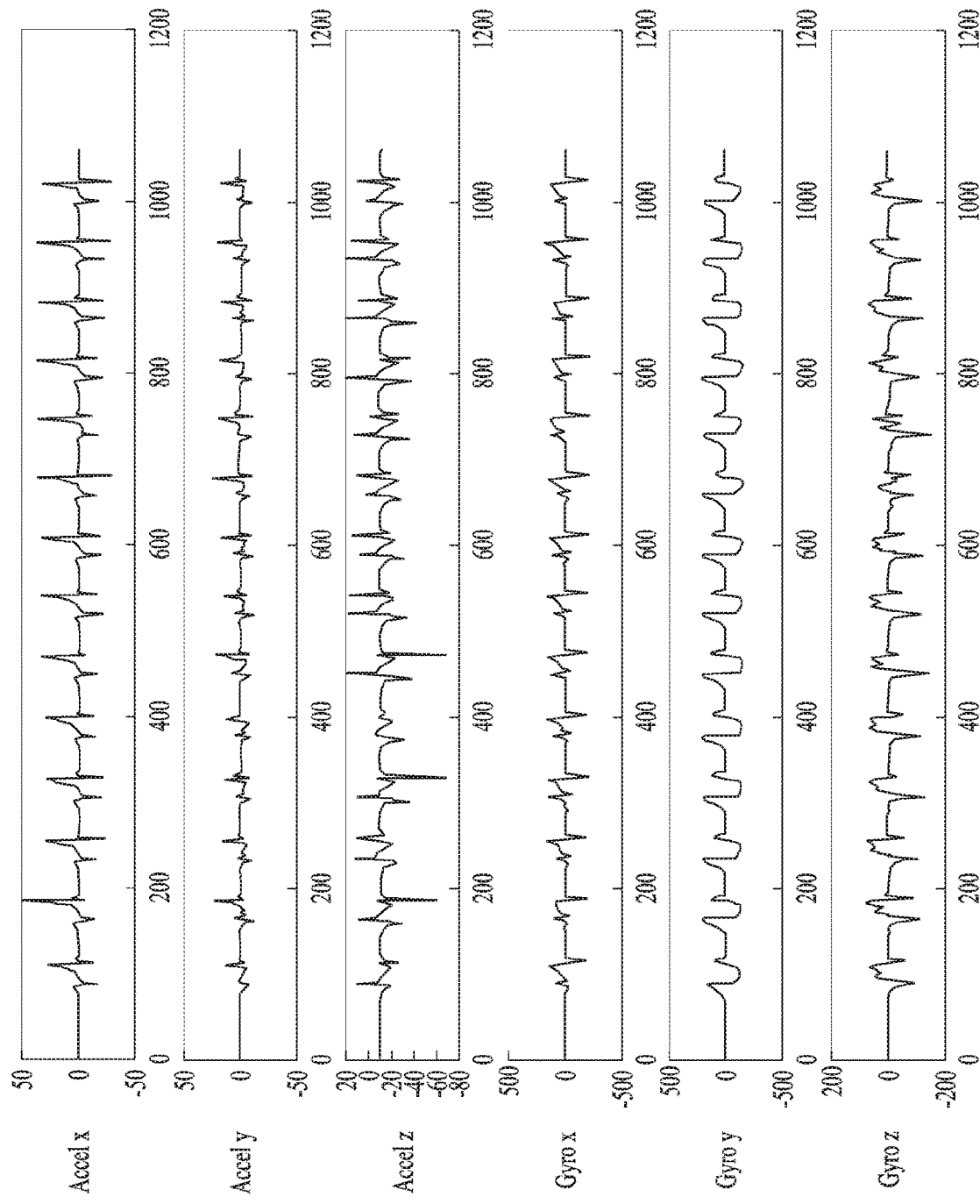
FIG. 25 is a pattern graph of sensing values sensed through an acceleration sensor of smart shoes with respect to flatland movement according to the present invention.
Figure 26:
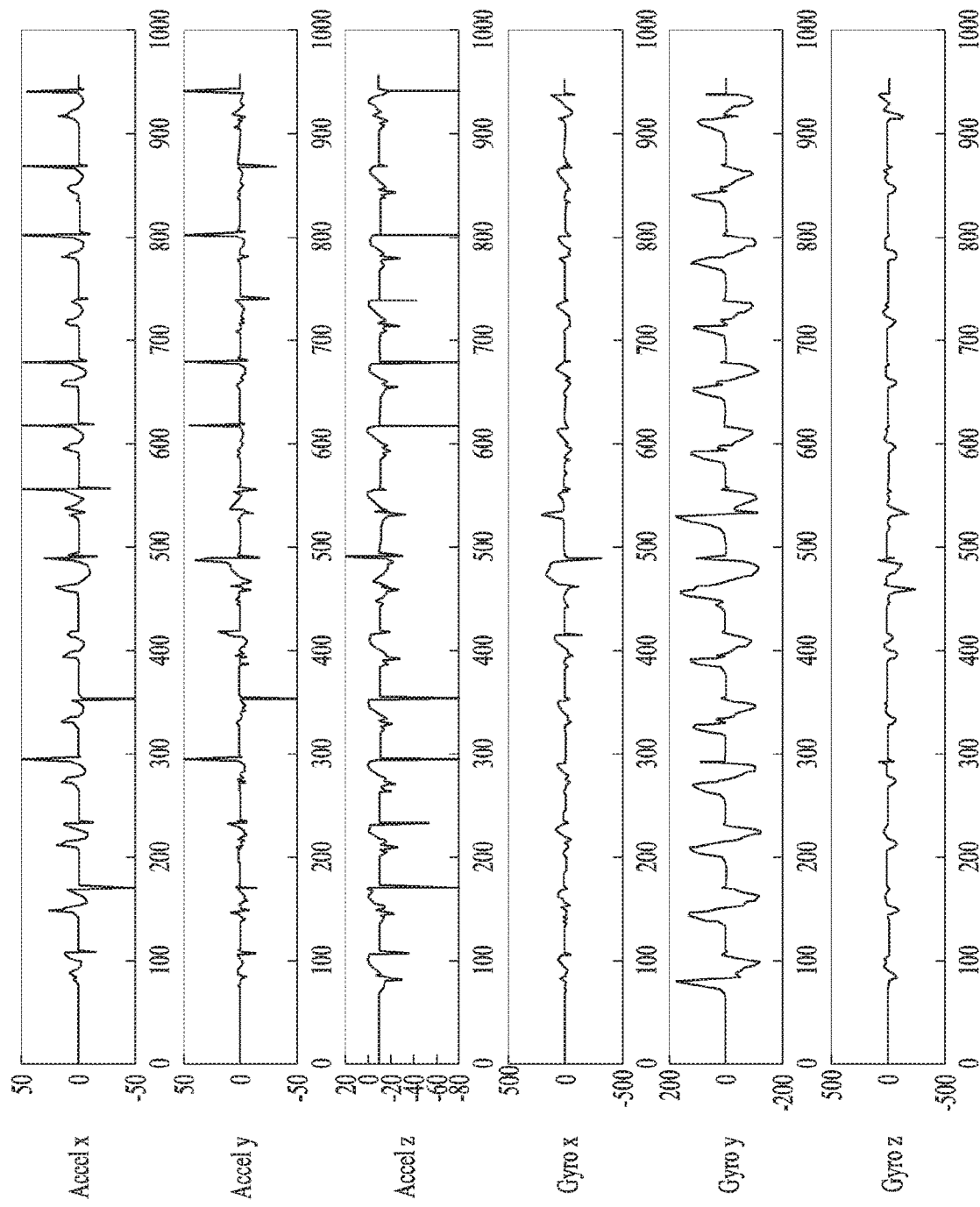
FIG. 26 is a pattern graph of sensing values sensed through an acceleration sensor of smart shoes with respect to stairs movement according to the present invention.

FIG. 25 is a pattern graph of sensing values sensed through an acceleration sensor of smart shoes with respect to flatland movement according to the present invention, and FIG. 26 is a pattern graph of sensing values sensed through an acceleration sensor of smart shoes with respect to stairs movement according to the present invention.

FIG. 25 illustrates a plot of sensing data sensed through three axes (x, y and z) of the acceleration sensor and three axes (x, y and z) of the gyro sensor of the smart shoes, that is, 6-axis sensor, with respect of the flatland movement.

FIG. 26 illustrates a plot of sensing data sensed through three axes (x, y and z) of the acceleration sensor and three axes (x, y and z) of the gyro sensor of the smart shoes, that is, 6-axis sensor, with respect of the stairs movement.

Referring to FIGS. 25 and 26, the flatland movement and the stairs movement of the smart shoes may be identified from each other using at least one of the acceleration sensor and the gyro sensor. Meanwhile, in the present invention, the flatland movement and the stairs movement of the smart shoes may be identified from each other using sensing data only of at least one of three axes of any one of the acceleration sensor and the gyro sensor. As another example, the flatland movement and the stairs movement of the smart shoes may be identified from each other sequentially using the 6-axis sensor of FIGS. 25 and 26. For example, the flatland movement and the stairs movement of the smart shoes may be identified from each other by comparing x-axis data of the acceleration sensor at the uppermost end of FIGS. 25 and 26. At this time, if it is determined that it is difficult to identify the flatland movement from the stairs movement by using x-axis data only of the acceleration sensor, the flatland movement and the stairs movement may be identified from each other by further comparing y-axis data of the acceleration sensor. In this way, the flatland movement and the stairs movement may be identified from each other by sequentially adding each of the sensing data of the 6-axis sensor. Meanwhile, a method determined in accordance with a system is used with respect to the order in selection of the acceleration sensor and the gyro sensor and the order in use of sensing data of a corresponding axis of the selected sensor. However, if the acceleration sensor is first used and x-axis or z-axis sensor is first used, the flatland movement and the stairs movement may be identified from each other more quickly and conveniently. However, the order is not limited to this case. Alternatively, as described above, if it is determined that it is difficult to identify the flatland movement from the stairs movement by using x-axis data only of the acceleration sensor, instead of the y-axis data of the acceleration sensor, a random axis sensing data of the gyro sensor may first be used. In other words, if it is difficult to identify the flatland movement from the stairs movement by using first axis sensing data of the first sensor, first axis sensing data of the second sensor may further be considered. In this way, predetermined axis sensing data of each sensor may be used alternately for identification of the stairs movement and the flatland movement.

In addition, if a sensor system included in the smart shoes has a power level of a predetermined level or less and for low power in accordance with a predetermined definition, at least one of the acceleration sensor, the gyro sensor and the pressure sensor may be used. For convenience, the acceleration sensor is used as an example in the present invention.

Through mutual comparison of FIGS. 25 and 26, it is noted that the flatland movement and the stairs movement may be identified from each other by a graph type only of each axis sensing data of each acceleration.

Figure 27:
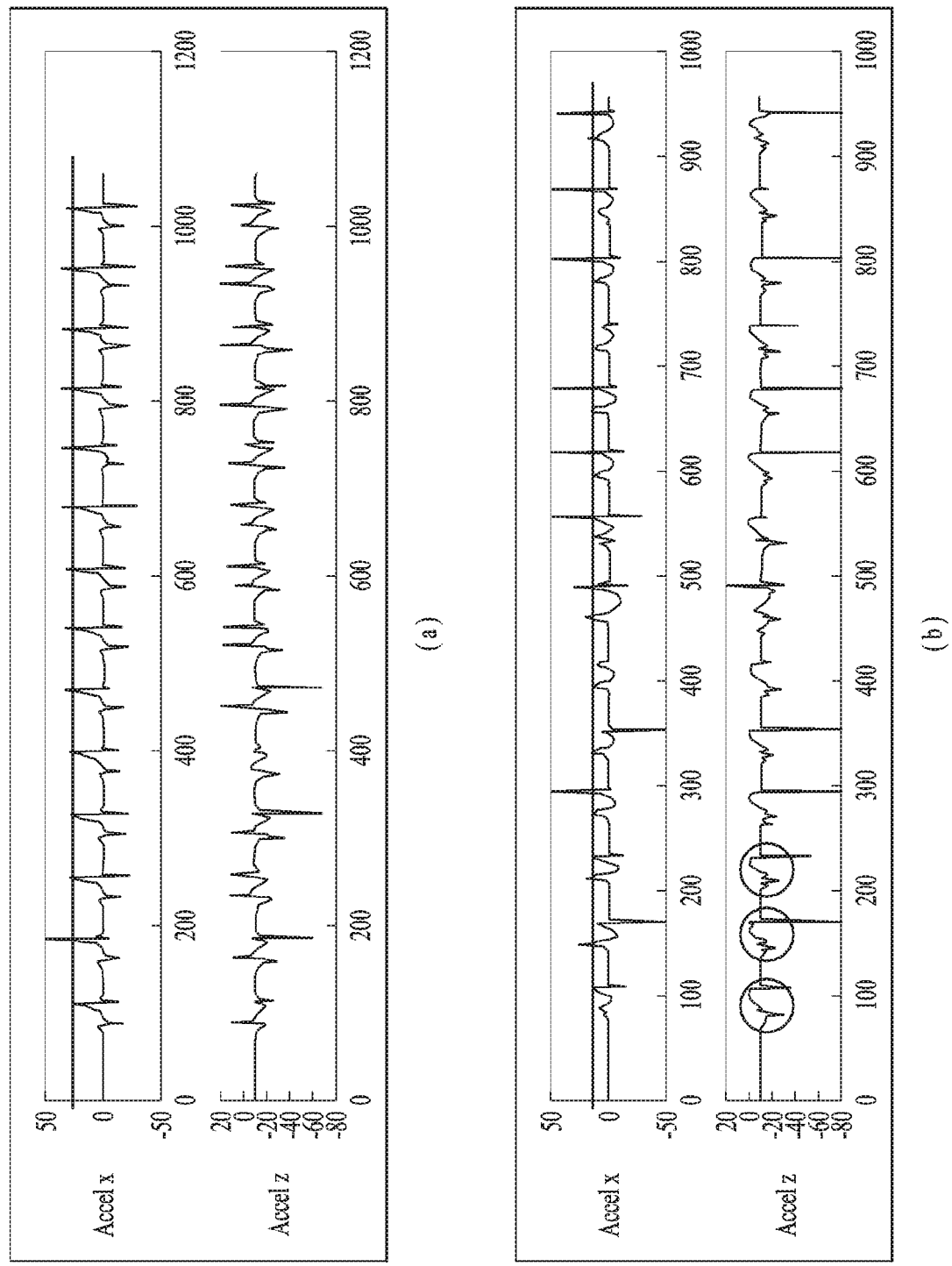
FIG. 27 is a view illustrating that sensing data of axes x and z of an acceleration sensor in FIGS. 25 and 26 are only extracted.

FIG. 27 is a view illustrating that sensing data of axes x and z of an acceleration sensor in FIGS. 25 and 26 are only extracted. Identification of the flatland movement and the stairs movement will be described in more detail with reference to FIG. 27.

FIG. 27a is an x-axis and z-axis sensing data graph of the acceleration sensor with flatland movement, and FIG. 27b is an x-axis and z-axis sensing data graph of the acceleration sensor with stairs movement. FIG. 27a may be identical to the data graph of FIG. 25, and FIG. 27b may be identical to the data graph of FIG. 26.

First of all, in comparing x-axis data of the acceleration sensor in respect of a stride, it is noted that the acceleration sensor value of FIG. 27b is smaller than the acceleration sensor value of FIG. 27a. In other words, it is noted that the acceleration x-axis value in flatland movement of FIG. 27a, that is, stride, is wider than the acceleration x-axis value in stairs movement of FIG. 27b. That is, the stride in the flatland movement is wider than that in the stairs movement.

Next, in comparing z-axis data of the acceleration sensor, it is noted that the acceleration sensor z-axis value of the stairs movement in FIG. 27b is different from the acceleration sensor z-axis value of the flatland movement in FIG. 27a in accordance with going up or down operation of stairs (circle marking parts of FIG. 27b). In other words, the acceleration sensor z-axis value relates to vertical movement of the user who wears the smart shoes. This means that the stairs movement has distinctive features as compared with the flatland movement.

Referring to FIG. 27, in the present invention, the flatland movement and the stairs movement of the user who wears the smart shoes may be identified from each other through x-axis and/or z-axis sensing data of the acceleration sensor provided in the smart shoes. The identified result may be transferred to an external device paired with the smart shoes to provide a related user interface. Therefore, the features of the z-axis sensing data of the acceleration sensor in the stairs movement may be extracted to recognize the stairs movement using machine learning. Alternatively, the x-axis peak value of the acceleration sensor may be used to recognize the stairs movement. This is based on that the stairs movement is different from the flatland movement in horizontal direction (x-axis) and vertical direction (z-axis).

Figure 28:
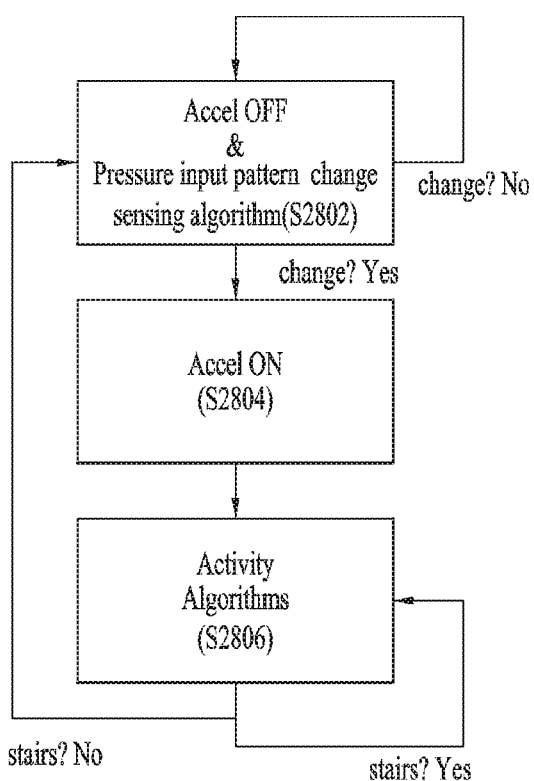
FIG. 28 is a flow chart illustrating a method for recognizing stairs movement according to one embodiment of the present invention.
Figure 29:
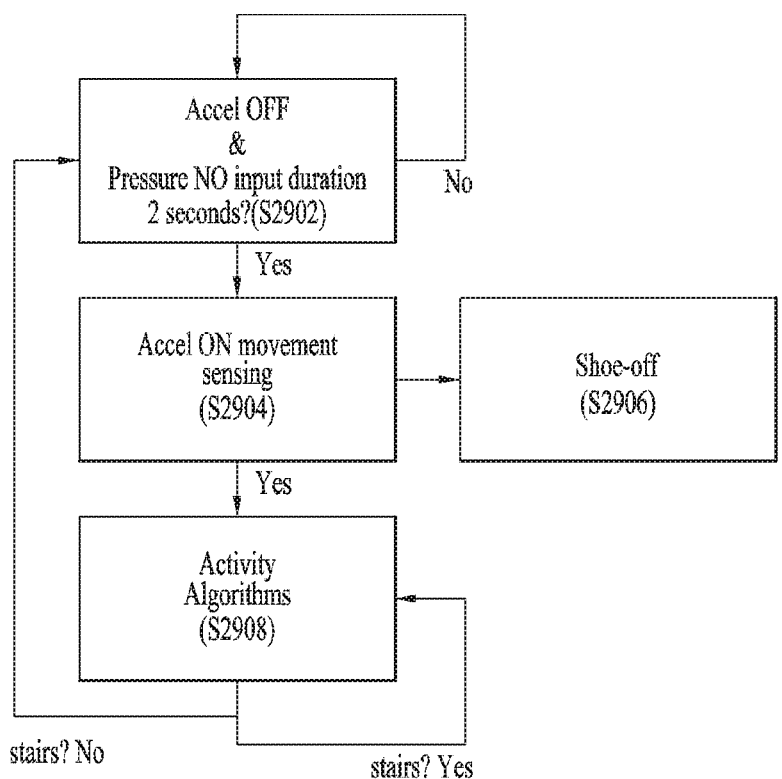
FIG. 29 is a flow chart illustrating a method for recognizing stairs movement according to another embodiment of the present invention.

FIG. 28 is a flow chart illustrating a method for recognizing stairs movement according to one embodiment of the present invention, and FIG. 29 is a flow chart illustrating a method for recognizing stairs movement according to another embodiment of the present invention.

In FIG. 28, the acceleration sensor in the smart shoes is implemented in the insole. In FIG. 29, the acceleration sensor is implemented in the midsole.

As described above, the acceleration sensor is used to recognize the stairs movement. However, in the flatland movement, the pressure sensor instead of the acceleration sensor may be used. Meanwhile, the user who wears the smart shoes does not always perform flatland movement or stairs movement only in the middle of wearing the smart shoes. The user who wears the smart shoes may perform flatland movement only at a predetermined time or perform stairs movement only at another predetermined time. However, if the acceleration sensor is always turned on by assuming this status, that is, considering stairs movement, it may be unfavorable for low power implementation which is one of issues of the smart shoes. Therefore, use of the acceleration sensor through recognition of the stairs movement will be described. Hereinafter, for understanding of the present invention and convenience of description, it is assumed that flatland movement is performed at a start point and then stairs movement is performed in FIGS. 28 and 29.

Referring to FIG. 28, the pressure sensor provided in the smart shoes is turned on, whereas the acceleration sensor is turned off. In this case, as described above, in the flatland movement, the pressure sensor receives and analyzes data of a step pattern of the user. The smart shoes determine whether there is a change of pressure sensor sensing data received through the pressure sensor as a result of analysis of the pattern (S2802).

The smart shoes continue to maintain the current state if there is no change of the pressure sensor sensing data as a result of analysis of the pattern. On the other hand, the smart shoes turn on the acceleration sensor to recognize the stairs movement if there is a change of the pressure sensor sensing data as a result of analysis of the pattern (S2804).

The smart shoes receive and analyze the acceleration sensor sensing data through the turned-on acceleration sensor (S2806).

As a result of the step S2806, if it is determined that the user who wears the smart shoes performs the stairs movement, the smart shoes control the acceleration sensor to continue to be turned on and receive and analyze stairs movement data of the user through the value sensed through the acceleration sensor. However, as a result of the determination, if it is determined that the user does not perform the stairs movement or another pattern different from the stairs movement data is found, that is, if there is a change of the data, the smart shoes may control the acceleration sensor which is turned on, to be turned off. At this time, the pressure sensor may continue to be turned on, and the acceleration sensor may be active by being turned on if it is turned off.

Next, referring to FIG. 29, the pressure sensor provided in the smart shoes is turned on, whereas the acceleration sensor is turned off. In this case, as described above, in the flatland movement, the pressure sensor receives and analyzes data of a step pattern of the user. The smart shoes determine whether the sensing data received through the pressure sensor are not input for a predetermined time (for example, 2 seconds) (S2902).

If the pressure sensor sensing data are not received continuously for a predetermined time, the smart shoes turn on the acceleration sensor to identify stairs movement (S2904).

At this time, the smart shoes determine whether the user has movement or has taken off the smart shoes, through the sensing value of the turned on acceleration sensor. In other words, if the sensing value of the turned on acceleration sensor is a predetermined threshold value or less or if there is no sensing value of the turned on acceleration sensor, the smart shoes may control the acceleration sensor to be again turned off by determining that the user has taken off the smart shoes (S2906).

However, if the acceleration sensor sensing data are received through the turned on acceleration sensor, the smart shoes receive and analyze the sensing data (S2908).

As a result of the step S2908, if it is determined that the user who wears the smart shoes performs stairs movement, the smart shoes control the acceleration sensor to be turned on and receive and analyze stairs movement data of the user through the value sensed through the acceleration sensor. However, as a result of the determination, if it is determined that the user does not perform the stairs movement or as a result of the analysis, if another pattern different from the stairs movement data is found, that is, if there is a change of the data, the smart shoes may control the acceleration sensor which is turned on, to be turned off. At this time, the pressure sensor may continue to be turned on, and the acceleration sensor may be active by being turned on if it is turned off.

FIG. 30 is a view illustrating a method for correcting movement of a user on the basis of data sensed through a sensor of smart shoes in accordance with one embodiment of the present invention.

In respect of the method for correcting movement of a user according to the present invention, a correct posture of stairs movement is that may maximize thigh strength exercise without damaging the back and knees. Therefore, in the present invention, a user interface may be configured to recognize whether a user who wears the smart shoes performs stairs movement at a correct posture through analysis from stairs movement sensing data and allow a user to exercise at the correct posture.

FIG. 30 relates to the pressure sensor according to the present invention. A case that the pressure sensors are uniformly distributed in the insole of the smart shoes will be described as an example.

In respect of stairs movement, FIG. 30a illustrates a correct movement posture, and FIG. 30b illustrates a movement posture which is not recommended. In other words, referring to FIG. 30a, it is noted that among the pressure sensors uniformly distributed in the smart shoes, the sensors corresponding to the front part are uniformly active. On the other hand, it is noted that some of the pressure sensors of the front part or all of the pressure sensors of the insole are active in FIG. 30b. In case of the latter case, it is noted that the user steps stairs using only a part of feet, that is, toe or sole. However, this is not recommended. This is because that the movement posture of FIG. 30b is not helpful for an exercise aspect and has likelihood of risk higher than that of FIG. 30a in view of an environmental aspect.

FIG. 31 is a view illustrating a comparison of sensing data through an acceleration sensor, a gyro sensor and a pressure sensor, which are implemented in smart shoes in accordance with one embodiment of the present invention.

FIG. 31a is a sensing data graph of the acceleration sensor and the gyro sensor when some sensors of the front part of the insole of the smart shoes are active as one of stairs movement posture, which is not recommended, based on the pressure sensor as shown in FIG. 30b. On the other hand, FIG. 31b is a sensing data graph of the acceleration sensor and the gyro sensor of the smart shoes corresponding to a correct stairs movement posture based on the pressure sensor as shown in FIG. 30a. Comparison between the sensing data graph of FIG. 31a and the sensing data graph of FIG. 31b is as follows.

Referring to FIG. 31a, it is noted that sensing data of the acceleration sensor and the gyro sensor are irregular at a stance of a predetermined point (circle marking part in the drawing). This is because that the user steps on the stairs using a part (for example, toe) of a foot based on the active pressure sensor. That is, it is noted that the user steps on next stairs using a right foot (R) in a state that the user steps on the stairs using only a toe of a left (L) foot, whereby likelihood of the irregular state is relatively high. This is because that the previous step does not support the next step sufficiently.

Referring to FIG. 31b, it is noted that sensing data of the acceleration sensor and the gyro sensor are regular without change at a stance of a predetermined point. This is because that the user may perform regular movement due to a sufficient support at a previous step. This is a correct movement on the stairs and becomes a recommended movement. This movement considers safety of the user together with an exercise aspect.

As described above, if the data of FIGS. 30 and 31 are sensed continuously, sufficient stairs movement data of the user are collected and then analyzed, whereby analysis resultant data of the stairs movement of the user may be fed back. The analysis resultant data may include correction data of the stairs movement of the user as well as activity amount obtained by the stairs movement.

FIG. 32 is a view illustrating one example of a user interface provided by a smart terminal on the basis of smart shoes data in accordance with one embodiment of the present invention.

For convenience, in FIG. 32, movement data of the user, which are sensed through the smart shoes, are provided through the user interface of a smart shoes application on a smart terminal such as a mobile terminal. However, the user interface may be provided in the form of voice.

FIG. 32a illustrates a screen on which a smart shoes application is executed in a smart terminal such as a mobile terminal, that is, a user interface screen of the smart shoes application.

Meanwhile, FIG. 32b illustrates an example of a user interface with respect to stairs movement in respect of the present invention, including data of a correct stairs movement ratio.

Figure 33:
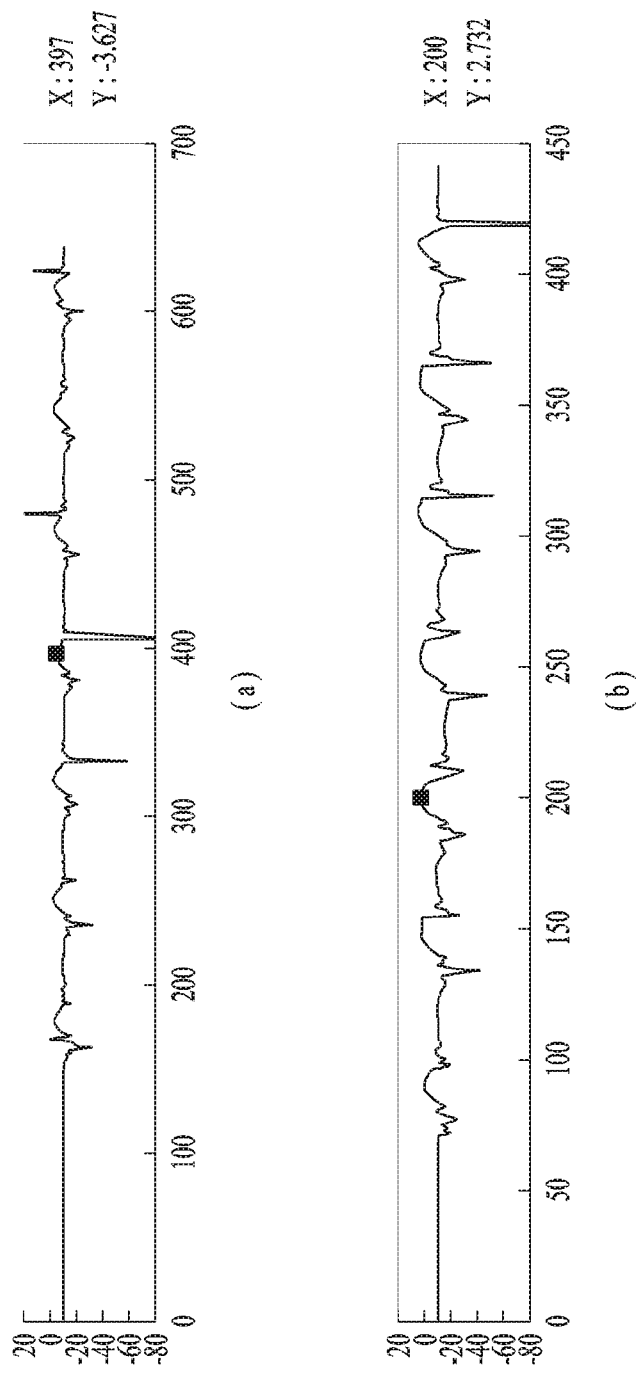
FIG. 33 is a view illustrating impact amount or activity amount in stairs movement according to one embodiment of the present invention.

FIG. 33 is a view illustrating impact amount or activity amount in stairs movement according to one embodiment of the present invention.

In respect of the present invention, activity amount with respect to the stairs movement is calculated differently from flatland movement. The stairs movement needs to be categorized into stairs movement of a normal step as shown in FIG. 33a and stairs movement of a powerful step as shown in FIG. 33b.

Generally, the user who wears the smart shoes considers total activity amount but may fail to consider counteraction according to the total activity amount. For example, the case of going up and down stairs at a normal step as shown in FIG. 33a and the case of going up and down stairs at a powerful step as shown in FIG. 33b may have respective data graphs different from each other even in case of the same stairs movement.

In the present invention, even in the case that movement of the user is determined as stairs movement, related impact amount data may be calculated with reference to a variable amount of z-axis of the acceleration sensor in FIGS. 33a and 33b. For example, if the variable amount of z-axis exceeds a predetermined threshold value, since a problem may occur when impact applied to a body of the user, especially knees is great or accumulated, a related notice may be performed. Also, a correlation and a weight value with respect to z-axis variable amount, impact amount and calorie of the acceleration sensor may be provided, whereby the activity amount in FIG. 33a and the activity amount in FIG. 33b may be calculated differently from each other even in case of the same stairs movement.

Meanwhile, in the present invention, recognition of the stairs movement, detection of impact amount, and calculation of activity amount have been described based on the data values sensed through the sensors provided in the smart shoes, such as the acceleration sensor, the pressure sensor and the gyro sensor. However, although not shown, the data values may be adjusted properly considering data of the user who wears the smart shoes. For example, sex, age, weight, remarks, etc. of the user may be reflected in the sensing data.

Figure 34:
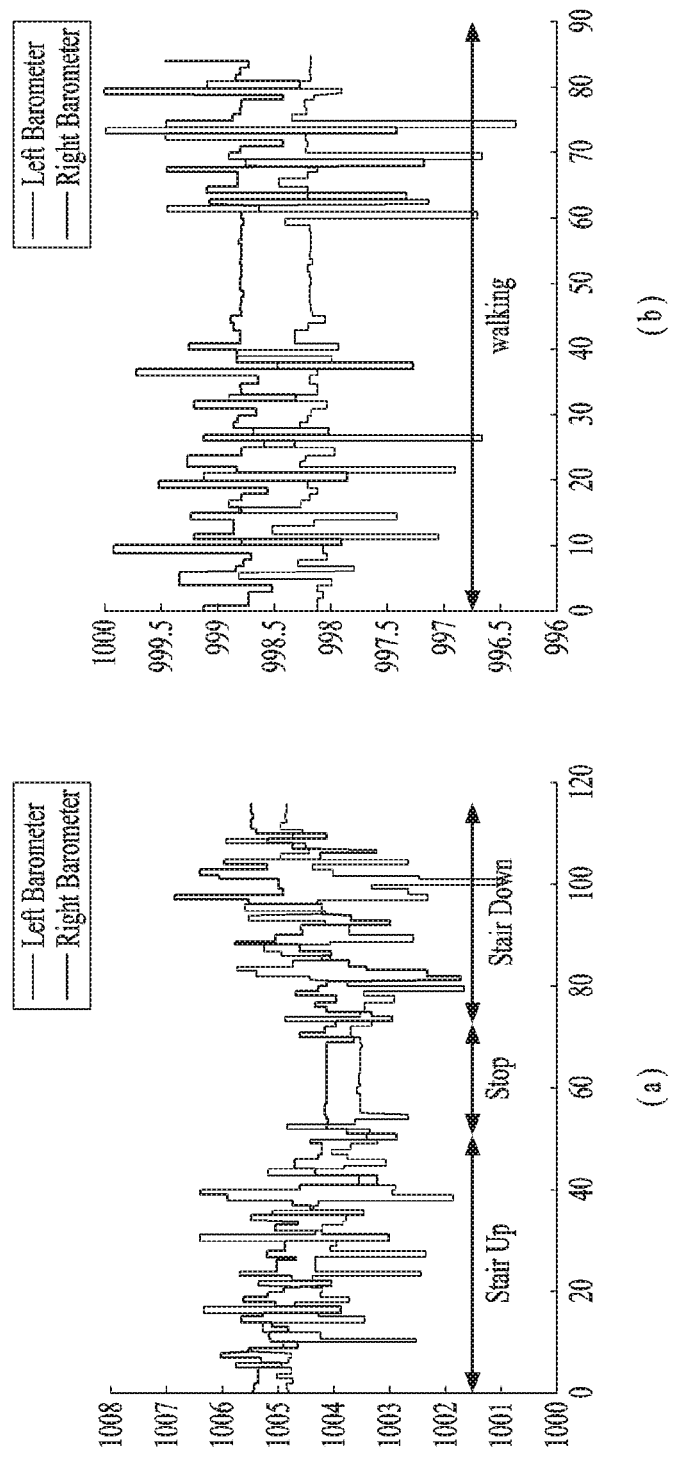
FIG. 34 is a view illustrating a method for sensing stairs movement according to another embodiment of the present invention.

FIG. 34 is a view illustrating a method for sensing stairs movement according to another embodiment of the present invention.

FIG. 34 relates to stairs recognition and velocity calibration data based on the barometer sensor. In FIG. 34, the barometer sensor is implemented in the insole of the smart shoes. However, the barometer sensor may be implemented in a smart device instead of the smart shoes.

FIG. 34a illustrates an example of a sensing data graph of a barometer sensor implemented in the smart shoes when the user who wears the smart shoes performs flatland movement, and FIG. 34b illustrates an example of a sensing data graph of the barometer sensor when the user who wears the smart shoes performs stairs movement.

As shown, the sensing data graph through the barometer sensor in the flatland movement of FIG. 34a and the sensing data graph through the barometer sensor in the stairs movement of FIG. 34b have data patterns different from each other, whereby the stairs movement and the flatland movement may be identified from each other. Meanwhile, since the barometer sensor is susceptible to other surrounding factors, reliability may be low. Therefore, the barometer sensor may be used as a factor for activation of the other sensors or may be used for the present invention by referring to or combination with data of the other sensors.

In addition, stairs movement velocity information may be provided from the data sensing pattern of FIG. 34b. For example, the stairs movement velocity information may be provided by combination of building interstory height of an indoor map, a variable amount of the barometer sensor, and insole time information. Meanwhile, if the barometer sensor is installed in the smart device not the smart shoes, the stairs movement velocity information may be used. In addition, if the barometer sensor is used, as described above, the barometer sensor may be used for interstory identification instead of recognition of every step. Therefore, the number of rough stories for stairs movement may be notified from the sensing data through the barometer sensor to the user, and information on consumed calories per story may be provided to the user. Also, the barometer sensor included in the smart shoes may perform filtering for a jumping part by applying a moving average even though noise is included therein through a pushed pressure of feet, whereby reliability of the data may be enhanced.

According to each or combination of the aforementioned various embodiments of the present invention, the movement data of activity of the user who wear the smart shoes may be calculated exactly, and the stairs movement and the flatland movement of the user who wears the smart shoes may be identified from each other, whereby the activity amount of the user may be calculated exactly. The movement data of the user who wears smart shoes may be detected exactly to calculate the activity amount, and motion guide data may be provided based on the detected movement data and the calculated activity amount, whereby satisfaction of the user may be improved and reliability of the smart shoes may be improved.

It will be apparent to those skilled in the art that the present invention may be embodied in other specific forms without departing from the spirit and essential characteristics of the invention. Thus, the above embodiments are to be considered in all respects as illustrative and not restrictive. The scope of the invention should be determined by reasonable interpretation of the appended claims and all change which comes within the equivalent scope of the invention are included in the scope of the invention.

What is claimed is:

1. A shoe comprising:
   a communication unit for transmitting and receiving a signal to and from an external device;
   a first sensor for sensing first movement data of a user who wears the shoe;
   a second sensor for sensing second movement data of the user;
   a memory for storing data sensed through the first sensor and the second sensor; and
   a controller for:
      turning on or off the second sensor based on the first movement data;
      sensing third movement data of the user through one of the first sensor and the second sensor in response to a request for pairing with the external device received via the communication unit from the external device;
      performing pairing with the external device through the communication unit based on the third movement data; and
      transmitting the first movement data and the second movement data to the paired external terminal through the communication unit.

2. The shoe according to claim 1, wherein the first movement data include flatland movement or slope movement of the user who wears the shoe, and the second movement data include stair movement of the user who wears the shoe.

3. The shoe according to claim 2, wherein the first sensor includes a pressure sensor, and the second sensor includes at least one of an acceleration sensor, a gyro sensor, a pressure sensor or a barometer sensor.

4. The shoe according to claim 1, wherein the controller controls the second sensor to be turned off when the first movement data are sensed through the first sensor.

5. The shoe according to claim 1, wherein the controller controls the second sensor to be turned on and sense the second movement data when a change in the first movement data is equal to or greater than a predetermined threshold value.

6. The shoe according to claim 1, wherein the controller controls the second sensor to be turned on and sense the second movement data when no first movement data are received through the first sensor for a predetermined time.

7. The shoe according to claim 6, wherein the controller:
   determines that the shoe is taken off when no data are sensed for a predetermined time after the second sensor is turned on; and
   turns off the second sensor.

8. The shoe according to claim 1, wherein the controller identifies the second movement data from the first movement data through sensing data of any one or combination axes of axes x, y and z of the second sensor.

9. The shoe according to claim 1, wherein the controller calculates second movement correction data of the user who wears the shoe through sensing data of any one or combination axes of axes x, y and z of the second sensor.

10. A terminal service system comprising a terminal and a shoe performing data communication with the terminal, the shoe comprising:
   a communication unit for transmitting and receiving a signal to and from the terminal;
   a first sensor for sensing first movement data of a user who wears the shoe;
   a second sensor for sensing second movement data of the user;
   a memory for storing data sensed through the first sensor and the second sensor; and
   a controller for turning on or off the second sensor based on the first movement data;
   sensing third movement data of the user through one of the first sensor and the second sensor in response to a request for pairing with the external device received via the communication unit from the external device;
   performing pairing with the external device through the communication unit based on the third movement data; and
   transmitting the first movement data and the second movement data to the paired external terminal through the communication unit, and
   the terminal configuring and outputting a user interface based on the first and second movement data transmitted from the shoe.

* * * * *